United States Patent [19]

Loskutoff et al.

[11] Patent Number: 4,791,068

[45] Date of Patent: Dec. 13, 1988

[54] DIAGNOSTIC ASSAY FOR INHIBITOR OF TISSUE-TYPE AND UROKINASE-TYPE PLASMINOGEN ACTIVATORS

[75] Inventors: David J. Loskutoff, Solana Beach; Raymond R. Schleef, San Diego, both of Calif.

[73] Assignee: Scripps Clinic and Research Foundation, La Jolla, Calif.

[21] Appl. No.: 623,357

[22] Filed: Jun. 22, 1984

[51] Int. Cl.$^4$ ............................................ G01N 33/543
[52] U.S. Cl. ...................................... 436/518; 435/7; 435/13; 436/545; 436/546
[58] Field of Search ....................... 435/7, 13, 172.2; 436/518, 545, 546

[56] References Cited

U.S. PATENT DOCUMENTS

| | | |
|---|---|---|
| 3,817,837 | 6/1974 | Rubenstein et al. |
| 3,996,345 | 12/1976 | Ullman et al. |
| 4,196,265 | 4/1980 | Koprowski et al. ............. 435/172.2 |
| 4,350,683 | 9/1982 | Galfre et al. .................... 435/172.2 |

OTHER PUBLICATIONS

Nanninga et al.–Chem. Abst., vol. 92 (1980) p. 36736n.
Golder et al.–Chem. Abst., vol. 100 (1984) p. 4341t.
Marchalonis and Warr, *Antibody as a Tool*, pp. 63 and 72, 1982.
Collen, *Thrombos. Haemostas*, 56:415–416 (1986).
Sprengers et al., *Blood*, 69:381–387 (1987).

*Primary Examiner*—Sam Rosen
*Attorney, Agent, or Firm*—Dressler, Goldsmith, Shore, Sutker & Milnamow, Ltd.

[57] ABSTRACT

A biochemical reagent system and methods for preparing and using same, as well as diagnostics utilizing the reagent system are disclosed. The biochemical reagent system comprises a receptor raised in an animal host to plasminogen activator inhibitor, and indicating means. The receptor binds to a specific plasminogen activator inhibitor that itself binds to tissue-type or urokinase-type plasminogen activators.

16 Claims, 19 Drawing Sheets

1  2  3

DIAGNOSTIC ASSAY FOR INHIBITOR OF TISSUE-TYPE AND UROKINASE-TYPE PLASMINOGEN ACTIVATORS

DESCRIPTION

1. Technical Field

The present invention relates to a biochemical reagent system including a receptor and an indicating means that recognizes and selectively binds to plasminogen activator inhibitors, and more particularly relates to biochemical reagent and diagnostic systems for the detection and quantitation of plasminogen activator inhibitors in blood and other biological samples.

2. Background of the Invention

Endothelial cells line the luminal surface of the vascular bed and are thought to play an active role in the specific proteolytic breakdown of locally deposited fibrin, Todd, J. Pathol. Bacteriol., 78, 281 (1959); Astrup, in Progress in Chemical Fibrinolysis and Thrombolysis, Davidson et al. eds., vol. 3, pp. 1–57, Raven Press, New York (1978). The potential of endothelium to initiate and control this process is emphasized by its capacity to synthesize and release plasminogen activators (PAs), Loskutoff et al., Proc. Natl. Acad. Sci. (U.S.A.), 74, 3903 (1977); Shepro et al., Thromb. Res., 18, 609 (1980); Moscatelli et al., Cell, 20, 343 (1980); Laug, Thromb. Haemostasis, 45, 219 (1981); Booyse et al., Thromb. Res., 24, 495 (1981), including both tissue-type and urokinase-type molecules, Levin et al., J. Cell Biol., 94, 631 (1982); Loskutoff et al., Blood, 62, 62 (1983). Endothelial cells may also produce inhibitors of fibrinolysis, Loskutoff et al., Proc. Natl. Acad. Sci. (U.S.A.), supra; Levin et al., Thromb. Res., 15, 869 (1979); Loskutoff et al., J. Biol. Chem., 256, 4142 (1981); Dosne et al., Thromb. Res., 12, 377 (1978); Emeis et al., Biochem. Biophys. Res. Commun., 110, 392 (1983); Loskutoff et al., Proc. Natl. Acad. Sci. (U.S.A.), 80, 2956 (1983); Levin, Proc. Natl. Acad. Sci. (U.S.A.), 80, 6804 (1983).

Although these inhibitors probably serve important regulatory roles in controlling the fibrinolytic system of the vascular wall, little is known about their specificity, mode of action, or biochemical nature. The conclusion that these inhibitors are actually synthesized by endothelial cells is obscured somewhat by recent reports that cultured cells may bind and internalize protease inhibitors from serum-containing culture medium, Cohen, J. Clin. Invest., 52, 2793 (1973); Pastan et al., Cell, 12, 609 (1977); Rohrlich et al., J. Cell Physiol., 109, 1 (1981); McPherson et al., J. Biol. Chem., 256, 11330 (1981).

The possibility of producing unlimited amounts of tissue-type plasminogen activator (t-PA) by recombinant DNA technology has generated much interest, both clinically and commercially. The conversion of the relatively inactive molecule into an extremely efficient thrombolytic agent by fibrin itself, suggests that t-PA may exist as an active enzyme only when localized to the fibrin-platelet thrombus itself. Thus, t-PA is considered to be a much more specific thrombolytic agent than urokinase-type plasminogen activator and streptokinase.

Tne interactions between t-PA and fibrin have raised the argument that natural inhibitors of t-PA are not necessary to regulate this system; i.e., regulation is achieved through the formation/dissolution of fibrin and, thus, do not exist. It is clear that the existence of such inhibitors in human blood would complicate attempts to design a specific, efficient, and safe thrombolytic program based upon genetically engineered t-PA. At the very least, calculations such as those of dose, treatment time and efficacy of treatment would be difficult to predict and/or monitor. This problem would be especially acute if inhibitor levels varied from individual to individual.

The existence of specific inhibitors of t-PA in plasma is a matter of some dispute, Collen, Thromb. Haemostas., 43, 77 (1980). In fact, it has been reported, Korninger et al., Thromb. Haemostas., 46, 662 (1981), that the activity of t-PA added to plasma had an in vitro half-life of 90 minutes as compared to an in vivo half-life of 2 minutes, Korninger et al., Thromb. Haemostas, 46, 658 (1981). Based upon these observations, those authors concluded that t-PA inhibition by plasma was physiologically unimportant.

That conclusion has recently been challenged in Kruithof et al., Prog. in Fibrinolysis, 6, 362 (1983). In Chmielewska et al., Thromb. Res., 31, 427 (1983), direct evidence was recently reported for the existence of a rapid inhibitor of t-PA in plasma. In all cases, this anti-t-PA activity was detected in the plasma of patients with or at risk to develop thrombotic problems; i.e., the very individuals most likely to receive t-PA therapy. This finding may account for the failure of Korninger et al., Thromb. Haemostas., supra, to detect such an activity since they only examined the plasma of "normal" individuals. To date, these reports on t-PA innibitors represent little more than qualitative descriptions of an "activity" detected in the blood of some individuals.

Recently, an antifibrinolytic agent in cultured endothelial cells was detected, Loskutoff et al., Proc. Natl. Acad. Sci. (U.S.A.), 80, 2956 (1983). This inhibitor is a major endothelial cell product and appears to be an inhibitor of plasminogen activator since it can neutralize the activity of both fibrin-independent (urokinase-type) and fibrin-dependent (tissue-type) plasminogen activators (PAs). The observation that human platelets contain an immunologically similar inhibitor, Erickson et al., Haemostasis, 14 (1), 65 (1984), that is released by them in response to physiologically relevant stimuli, e.g., thrombin, and in parallel with other platelet proteins, e.g., Platelet Factor 4, emphasizes the potential importance of this inhibitor in human biology.

The inhibitor found by Loskutoff et al., supra, was purified from bovine aortic endothelial cell conditioned media by a combination of concanavalin A affinity chromatography and preparative sodium dodecyl sulfate-polyacrylamide gel electrophoresis (SDS-PAGE), and was shown to be a single chain glycoprotein of a molecular weight of 50,000 daltons, having an isoelectric point of 4.5–5.

SUMMARY OF THE INVENTION

The present invention contemplates a biochemical reagent system and methods of preparing and using same, as well as diagnostics utilizing the reagent system. The biochemical reagent system comprises (a) a receptor such as an antibody raised in an animal host to a plasminogen activator inhibitor; i.e., an anti-plasminogen activator, and (b) an indicating means.

In one aspect of the invention, the biochemical reagent system is comprised of (a) an indicating means and (b) a receptor that may be a polyclonal antibody raised in an animal host. The indicating means and receptor may be a single molecule or may be composed of a plurality of individual molecules. The receptor binds to a specific plasminogen activator inhibitor that itself binds to and inhibits tissue-type or urokinase-type plasminogen activator. The indicating means labels the receptor, and in so doing indicates the presence of the inhibitor in a sample to be assayed such as serum of patients having thrombotic disease. The receptor of the reagent system of the present invention selectively binds to inhibitor bound to tissue-type (t-PA) and urokinase-type (u-PA) plasminogen activators.

In another aspect of the present invention, a method of forming a polyclonal receptor for use in a biochemical reagent system is contemplated. The method comprises the steps of: (a) administering to an animal host a plasminogen activator inhibitor in an amount sufficient to induce the production of antibodies to the inhibitor, the antibodies being a receptor for said inhibitor; (b) collecting antisera containing said antibodies from the immunized host; and (c) recovering the receptor from the antisera.

Yet another aspect of the present invention relates to a method of forming a biochemical reagent system. The method comprises the steps of forming the polyclonal receptor described above as steps (a)–(c) with an additional step (d) of combining the receptor with an indicating means.

Both of the above methods can also include the step of administering to the host after step (a) and a sufficient period of growth, e.g., 1–2 weeks, but before step (b), a second injection of the same inhibitor to boost the production of antibody.

The present invention also includes polyclonal receptors produced by the above described method.

In a further aspect of the present invention a solid phase assay method of detecting the presence and quantity of plasminogen activator inhibitor in a sample to be assayed is contemplated. The method comprises the steps of: (a) providing a solid matrix on which to assay said sample; (b) affixing on said solid matrix a binding reagent that binds to (complexes with) said inhibitor to form a solid phase support, said binding reagent being a plasminogen activator selected from the group consisting of t-PA and u-PA or the above described polyclonal receptor; (c) admixing an aliquot of a liquid sample to be assayed with the solid phase support to form a solid-liquid phase admixture; (d) maintaining the admixture for a predetermined time sufficient for the binding reagent to bind to (complex with) inhibitor present in the sample; (e) separating the solid and liquid phases; and (f) determining the presence of inhibitor that bound to (complexed with) the binding reagent.

In preferred practice, the quantity of inhibitor bound to the binding reagent is determined by (i) admixing an aqueous liquid solution of second binding reagent that binds to the inhibitor bound on the solid support with the solid phase obtained after step (e) above to form a second solid-liquid phase admixture, the second binding reagent complexing with the inhibitor,; (ii) maintaining the second solid-liquid admixture for a predetermined time sufficient for the second binding reagent to bind (form a complex) with the inhibitor (typically about 2 to about 4 hours); (iii) separating the solid and liquid phases of the second solid-liquid phase admixture; and (iv) determining the quantity of the second binding reagent that bound to the inhibitor, and thereby determining the quantity of inhibitor.

The present invention further includes a mammalian diagnostic system such as a kit. The kit includes at least one package containing as an active ingredient the biochemical reagent system of this invention and t-PA or u-PA. The biochemical reagent system comprises a polyclonal receptor in dry, solution, or dispersion form, that, when admixed with an indicating means and a sample to be assayed, binds selectively to t-PA inhibitor present in the sample and indicates the presence and amount of the inhibitor. Indicating groups that may be contained in the system include a radioactive element, a biologically active enzyme, or an NMR-active element.

The diagnostic system may also include a solid matrix that may be a microtiter strip such as that containing twelve wells in a row. The t-PA or u-PA present is preferably bound to the solid matrix.

The diagnostic system may further include a standard against which to compare the assay results, as well as various buffers in dry or liquid form, for, inter alia, washing the wells, diluting the sample or diluting the labeled reagent.

The use of a biochemical reagent system of this invention includes the detection and quantitation of a specific plasminogen activator inhibitor that is bound to (complexed with) a plasminogen activator such as tissue-type or urokinase-type plasminogen activator. An especially preferred use of such a reagent system relates to the detection of plasminogen activator inhibitor in an in vitro protocol.

The present invention provides several benefits and advantages.

One benefit of the present invention is that the biochemical reagent system and diagnostic system of the invention are highly specific. Biological samples frequently contain numerous fibrinolytic inhibitors. It is difficult to distinguish among them by existing assays since those assays, in general, measure the capacity of a sample to decrease the activity of plasminogen activators or plasmin. In contrast, the particularly preferred diagnostic system of the present invention detects only inhibitor bound to particular plasminogen activators.

Another benefit of the present invention is that the reagent system of the invention is quantitative, providing a measure of the quantity of functionally active inhibitor bound to PAs, and not inhibitor activity. Therefore, the reagent system may not be as influenced by changes in salt or pH, for example, as are enzymatic assays.

One of the advantages of the present invention is that the diagnostic system of the invention may employ tissue-type plasminogen activator (t-PA) or urokinase-type plasminogen activator (u-PA) bound to wells of microtiter plates, and thus readily lends itself to screening large numbers of samples in a rapid and reproducible manner.

Another advantage of the present invention is that the biochemical reagent system and diagnostic system of the invention measure only functionally active inhibitor; i.e., inhibitor that binds to t-PA or u-PA. It is this form that is likely to change in various diseases. The inhibitor, as released by endothelial cells and platelets, exists in two forms, one active, and one inactive. The inactive form can be activated by treatment with denaturants, such as SDS and guanidine. Thus, an added advantage of the reagent and diagnostic systems of the present invention is that they can be used to measure the relative amount of both active and inactive inhibitor in various samples.

Other advantages and benefits of the present invention will become readily apparent to those skilled in the art from the following description of the invention, the drawings and the appended claims.

BRIEF DESCRIPTION OF THE DRAWINGS

In the drawings forming a portion of the disclosure of this invention.

$^{125}$I-plasminogen was added, and the incubation continued for another 60 minutes. The reaction was stopped by heating the samples at 100° C. for 3 minutes in the presence of 3 percent SDS and 5 percent 2-mercaptoethanol. The ability of the various samples to cleave the $^{125}$I-plasminogen into its characteristic heavy and light chains was assessed by SDS-PAGE and autoradiography as in Mussoni et al., Thromb. Res., 34, 241 (1984). Quantitation was achieved by excising the $^{125}$I-labeled plasminogen and plasmin chains from the dried gel, and counting them in a gamma counter. The data are expressed as a percentage of plasminogen cleavage observed in the absence of inhibitor.

Figure 5:
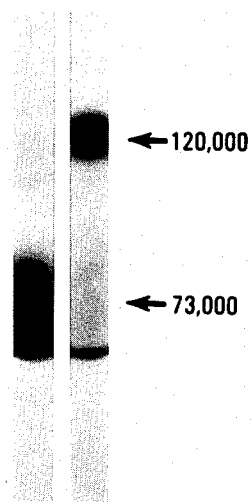

FIG. 5 is a photocopy of an autoradiogram showing the binding of $^{125}$I-labeled t-PA to the BAE inhibitor. $^{125}$I-labeled t-PA was incubated for 30 minutes at 37° C. in the absence (lane 1) or presence (lane 2) of the purified inhibitor (1 microgram/ml). The reaction was stopped by the addition of sample buffer, and the samples were then analyzed by SDS-PAGE and autoradiography.

Figure 6:
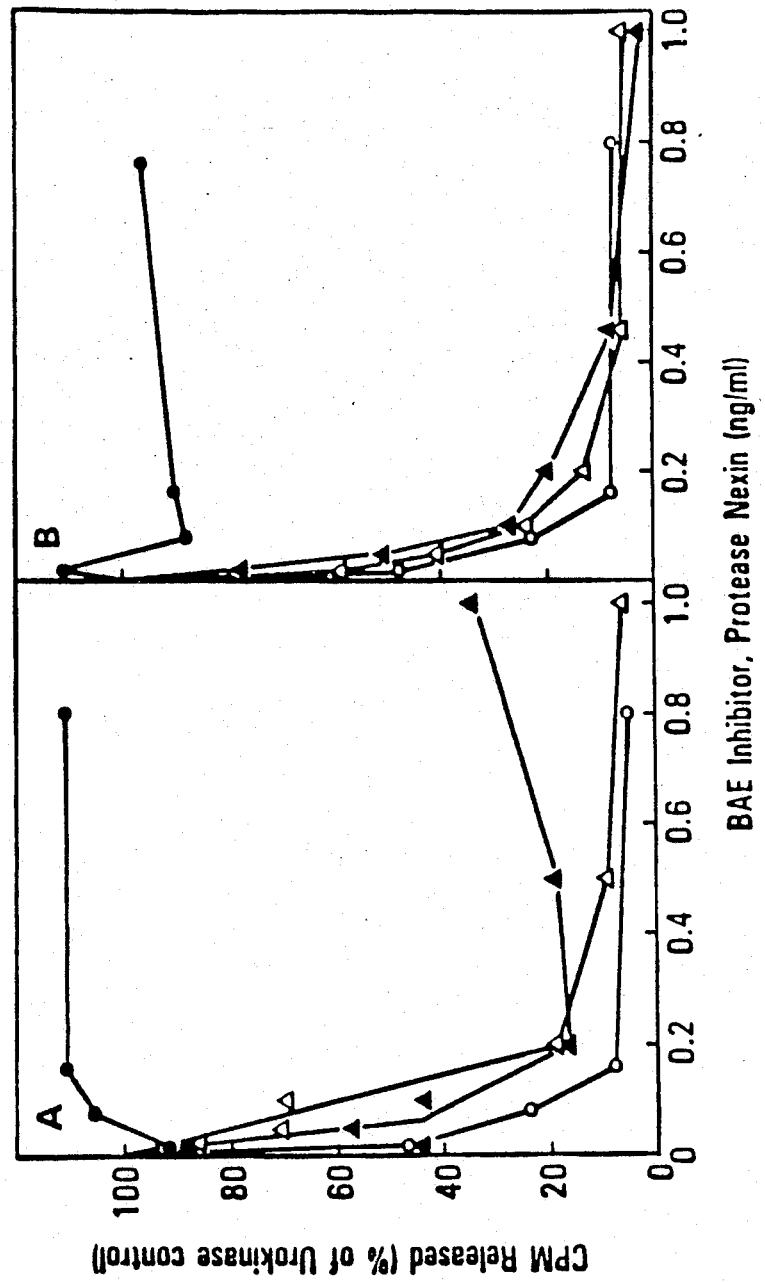

FIG. 6 is a graph illustrating the relative stabilities of the BAE inhibitor and protease nexin. Purified inhibitor (20 micrograms/ml) and purified protease nexin (160 micrograms/ml) were incubated for 60 minutes at 37° C. at pH 2.7 (A) or in the presence of 0.025 percent SDS (B) as described in detail hereinafter. The samples were neutralized by the addition of three volumes of assay buffer, diluted into assay buffer, and tested for residual inhibitor activity by the $^{125}$I-fibrin plate assay (described hereinafter). In control experiments, PBS was substituted for glycine and SDS, respectively. The data are expressed as the percentage of u-PA controls lacking inhibitor. The samples tested included untreated (○) and treated (●) protease nexin, and untreated (△) and treated (▲) BAE inhibitor.

Figure 7:
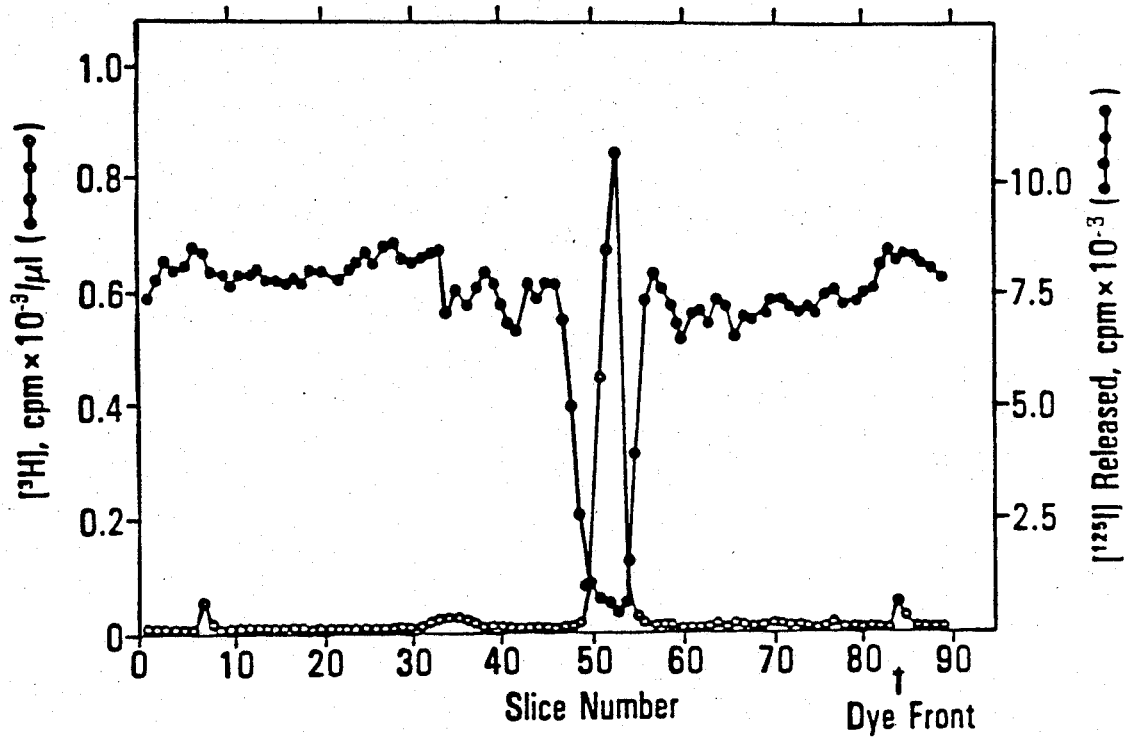

FIG. 7 is a graph illustrating SDS-PAGE of L[3,4,5-$^3$H] leucine labeled concanavalin A fraction II. An aliquot (225 microliters) of the concanavalin A peak II sample was subjected to SDS-PAGE in tube gels. After electrophoresis, the gel was sliced and each of the slices was extracted into buffer as described in detail hereinafter. The resulting gel extracts were tested for inhibitor activity by the $^{125}$I-fibrin plate method (●) and for radioactivity by scintillation counting (○) as described hereinafter.

Figure 8:
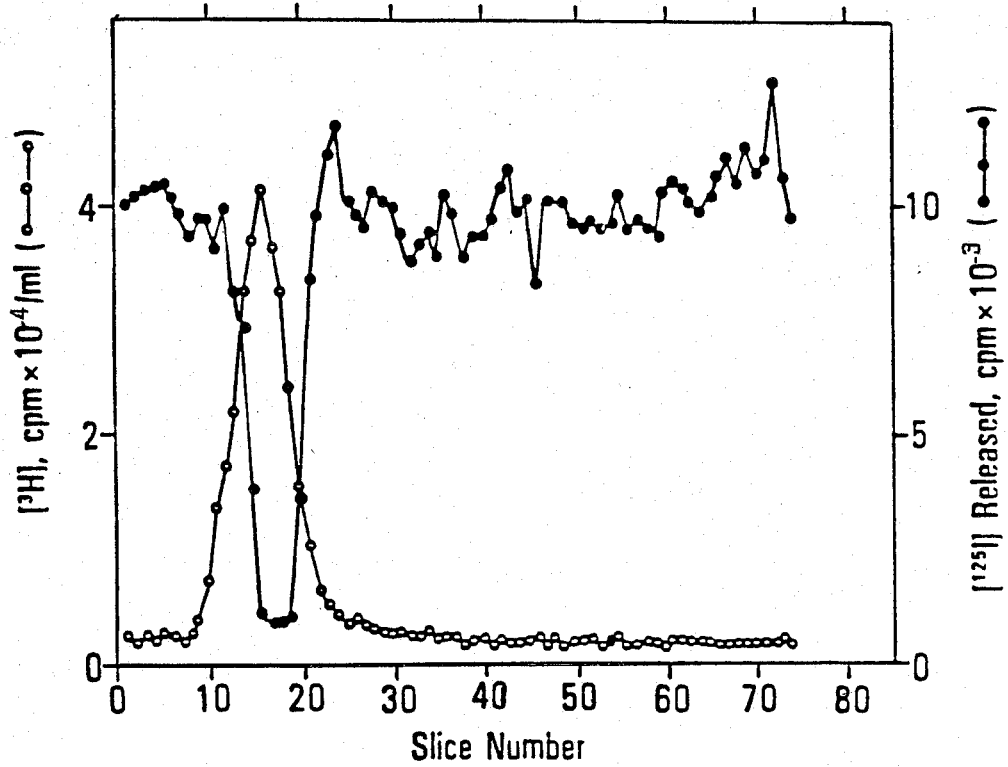

FIG. 8 is a graph illustrating alkaline PAGE of L[3,4,5-$^3$H] leucine labeled inhibitor extracted from SDS gels. The inhibitor fractions after SDS-PAGE (slice extracts 51-54, as shown in FIG. 7) were pooled, combined with albumin to a final concentration of 100 micrograms/ml, and dialyzed against PBS containing 0.5 percent Triton X-100. The sample was then fractionated by alkaline PAGE in tube gels and processed for the determination of radioactivity (○) and inhibitor activity (●) as described above for FIG. 7.

Figure 9:
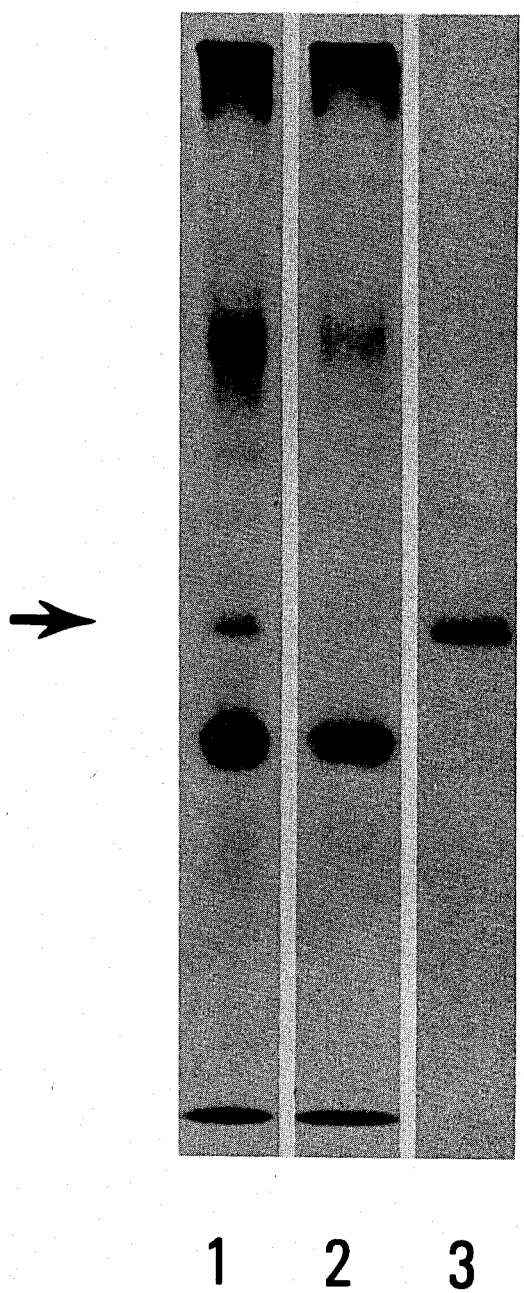

FIG. 9 is a photocopy of an autoradiogram showing immunoprecipitation of inhibitor from CM. L[3,4,5-$^3$H] leucine labeled CM from cloned BAEs was incubated with Protein A-Sepharose beads containing antiserum to purified inhibitor as described in detail hereinafter. The immobilized complexes were extracted from the beads by incubation for 1 hour at 37° C. with 0.25M Tris, 2.2 percent SDS, 2.5 percent (v/v) 2-mercaptoethanol, and 20 percent glycerol (pH 6.5). The extracts were fractionated by SDS-PAGE on slab gels and examined by autoradiography. Lane 1 shows starting material (CM); lane 2 shows immunosupernatant; lane 3 shows immunoprecipitate. The arrow indicates the position of inhibitor activity as revealed by reverse fibrin autography (not shown).

Figure 10:
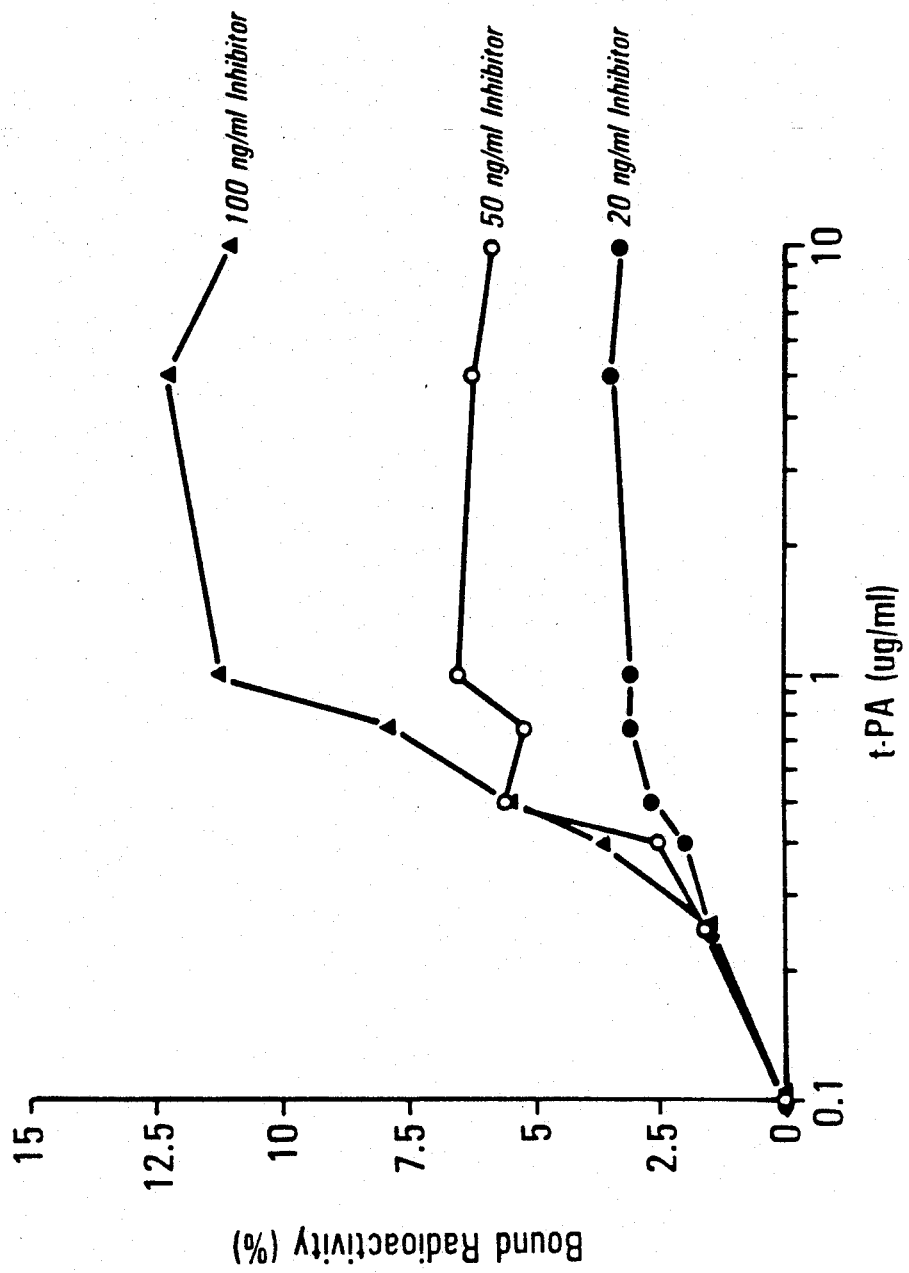

FIG. 10 is a graph illustrating the binding of purified inhibitor to microtiter wells coated with varying concentrations of t-PA. Polyvinyl chloride (PVC) plastic wells were incubated for about 18 hours at 4° C. with t-PA in phosphate-buffered saline (PBS) (50 microliters/well) at the indicated concentrations in units of micrograms/milliliter (μg/ml). The wells were washed, blocked with bovine serum albumin (BSA), and incubated for 2 hours with purified inhibitor in dilution buffer: 20 nanograms (ng)/ml, ●---●; 50 ng/ml, ○---○; 100 ng/ml, △----△. After washing the wells, the bound inhibitor was detected by incubation for 2 hours at 37° C. with rabbit anti-inhibitor receptor (1:100 dilution), followed by a 2 hour incubation at 37° C. with $^{125}$I-goat anti-rabbit IgG ($1.5 \times 10^5$ cpm/well). The bound radioactivity in each of the individual wells was determined in a gamma counter and is shown as a percentage of that offered for binding.

Figure 11:
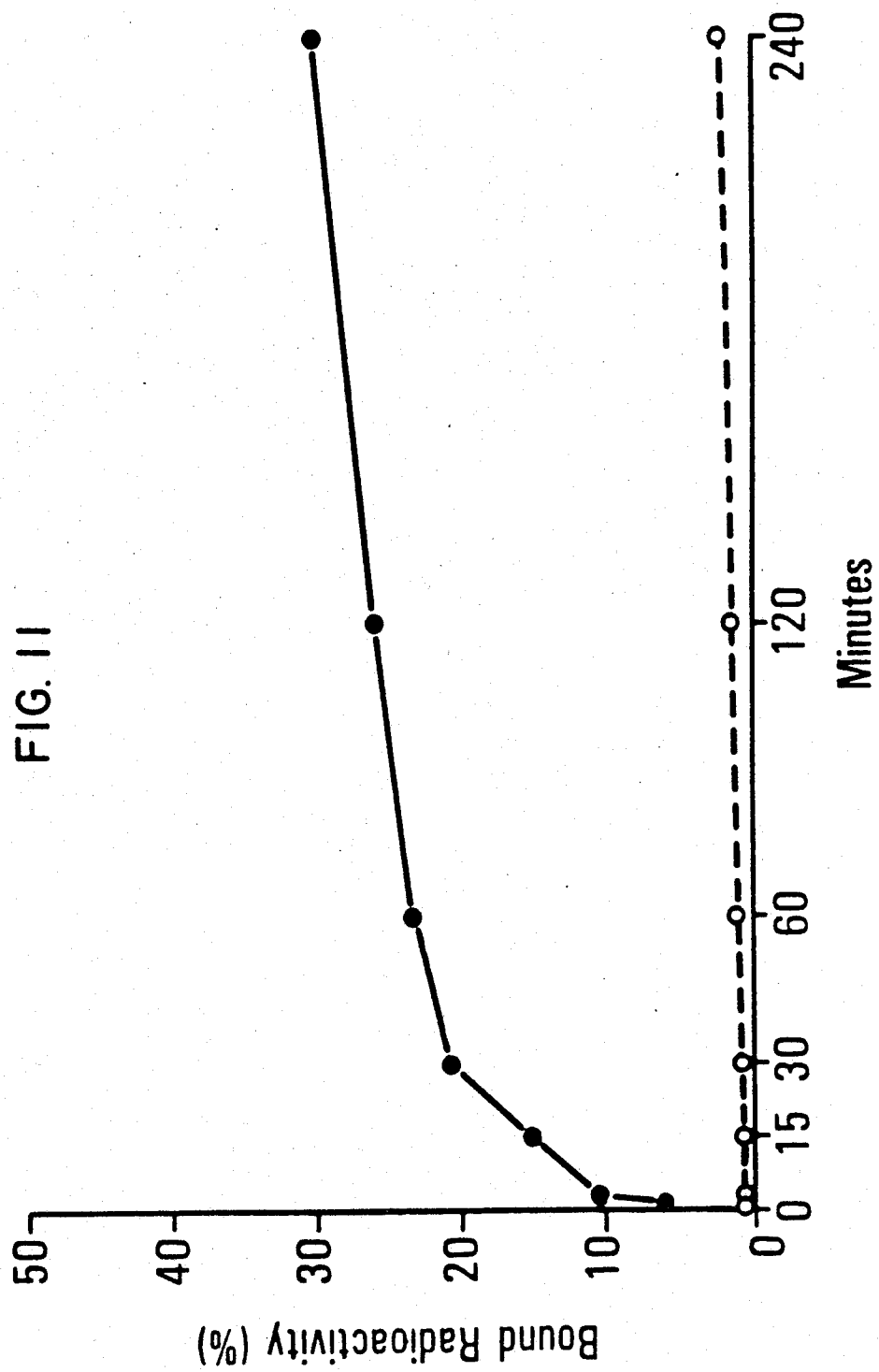

FIG. 11 is a graph illustrating the kinetics of inhibitor binding to t-PA coated wells. PVC plastic wells were incubated overnight at 4° C. with 50 microliters of either t-PA (1 ng/ml in PBS, ▼ ●) or BSA (1 ng/ml in PBS,◻ ○). The wells were washed, blocked with BSA, and incubated at 37° C. for the indicated times with purified inhibitor (100 ng/ml) in dilution buffer. After washing the wells, the bound inhibitor was detected as indicated for FIG. 10.

Figure 12:
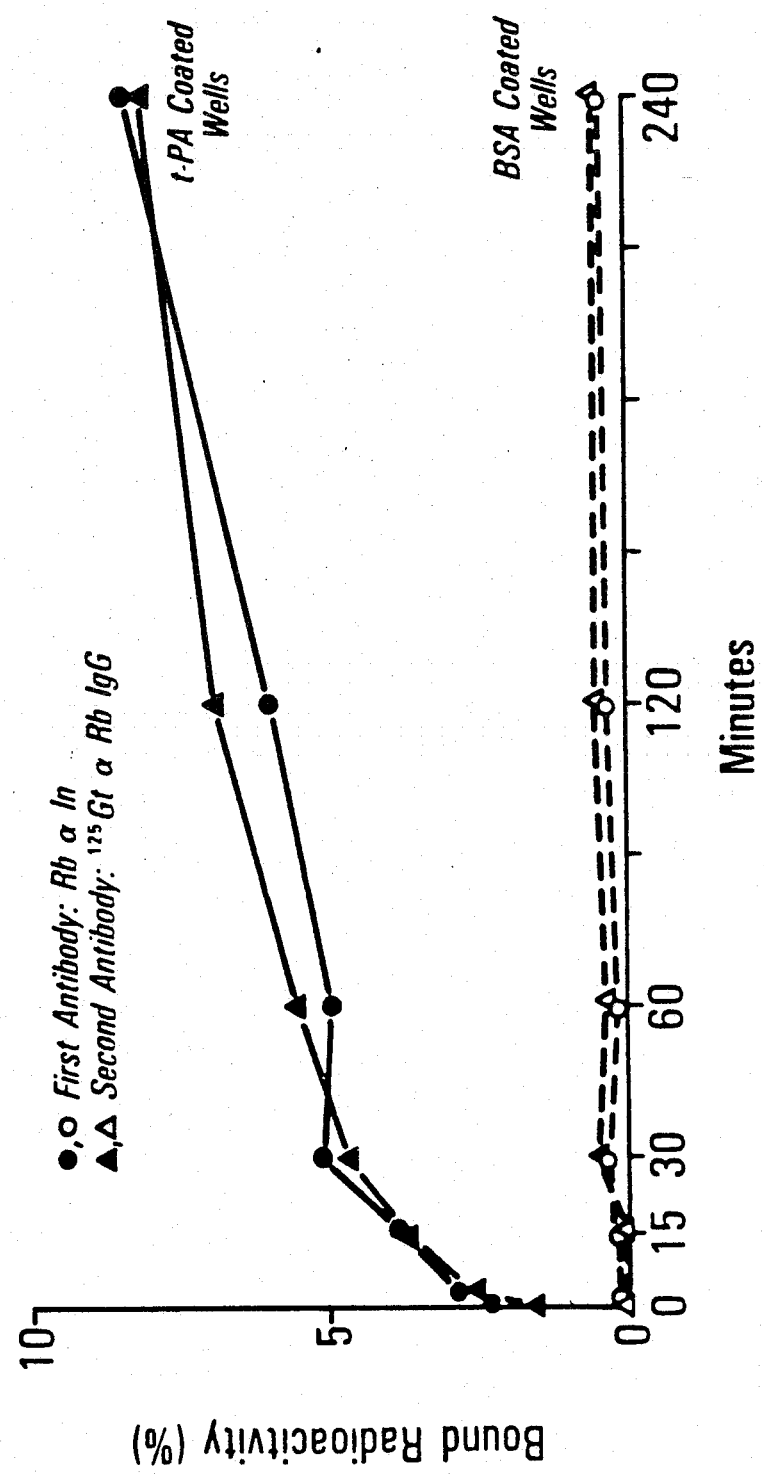

FIG. 12 is a graph illustrating the effect of incubation time of either first or second antibody on the detection of purified inhibitor. PVC plastic wells were coated with t-PA (closed figures) or BSA (open figures), washed, blocked and incubated for 1 hour with the purified inhibitor (50 ng/ml) as described for FIG. 10. The wells were incubated with rabbit anti-inhibitor receptor (RbaIn) (1:100 dilution, ○, ●) for the indicated times followed by a 2 hour incubation with $^{125}$I-goat anti-rabbit IgG ($^{125}$GtaRb IgG) ($1.5 \times 10^5$ cpm/well). Alternatively, the wells were incubated for 2 hours with rabbit anti-inhibitor receptor and the incubation time of $^{125}$I-goat anti-rabbit IgG (△, ▲) was varied.

Figure 13:
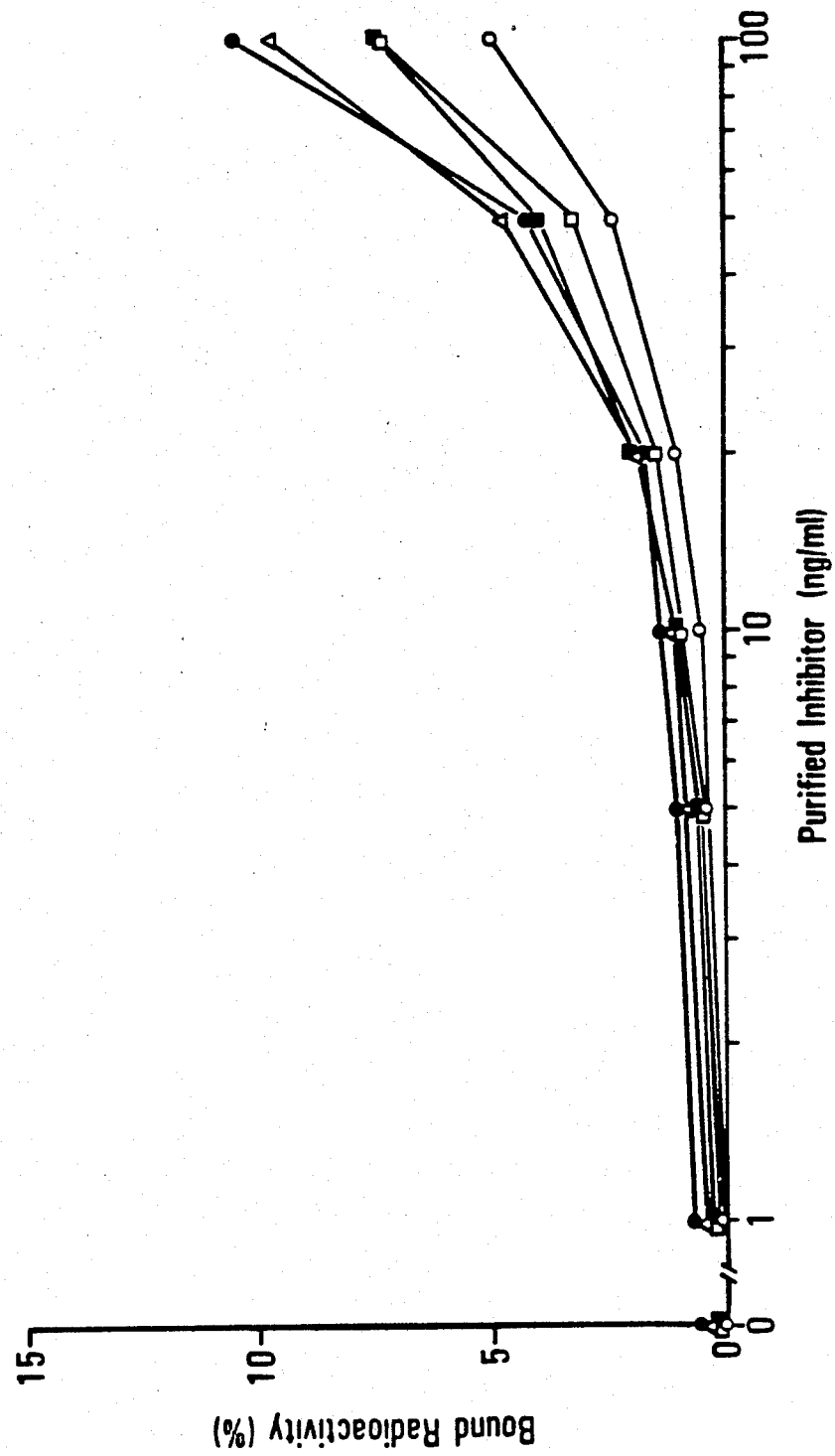

FIG. 13 is a graph illustrating the effect of varying amounts of rabbit anti-inhibitor receptor on the detection of purified inhibitor. PVC plastic wells were coated with t-PA, washed, blocked, and incubated with the inhibitor (50 ng/ml) in the amounts shown as described for FIG. 10. The wells then were incubated for 2 hours at 37° C. with rabbit anti-inhibitor receptor at various dilutions (1:50, ●; 1:75, △; 1:100, ■; 1:200, ◻; 1:500, ○). The bound antibody-inhibitor-t-PA complex was detected as described for FIG. 10.

Figure 14:
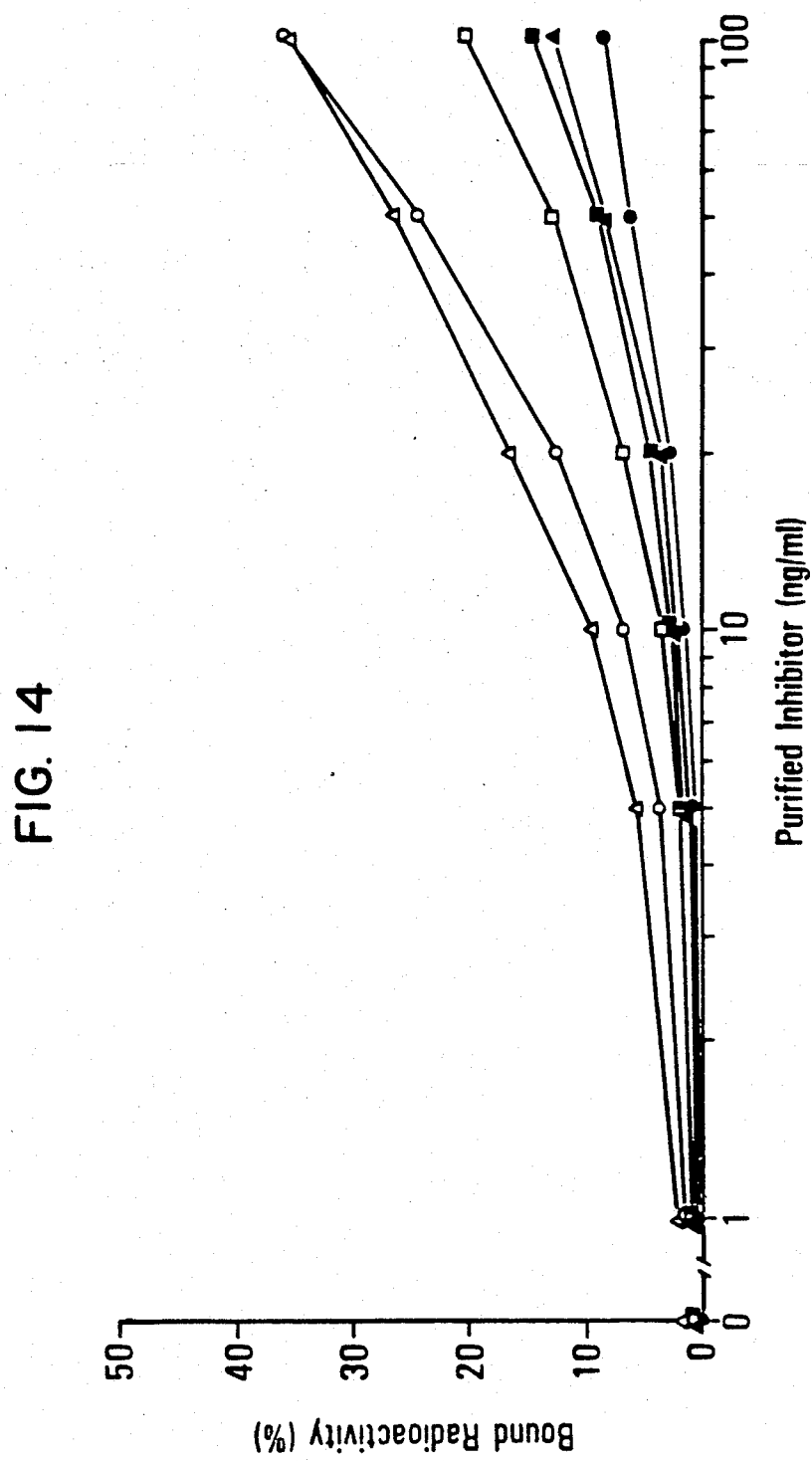

FIG. 14 is a graph illustrating the effect of varying amounts of $^{125}$I-goat anti-rabbit IgG on the detection of purified inhibitor. PVC plastic wells were coated with t-PA, washed, blocked and incubated with the inhibitor (50 ng/ml) as described for FIG. 10. The wells were incubated for 2 hours at 37° C. with the rabbit anti-inhibitor receptor (1:75). After washing, the wells were incubated for 2 hours at 37° C. with $2.5 \times 10^4$ (△), $5 \times 10^4$ (○), $1 \times 10^5$ (◻), $1.5 \times 10^5$ (■), $2 \times 10^5$ (▲), $3 \times 10^5$ (●) cpm of $^{125}$I-goat anti-rabbit IgG.

Figure 15:
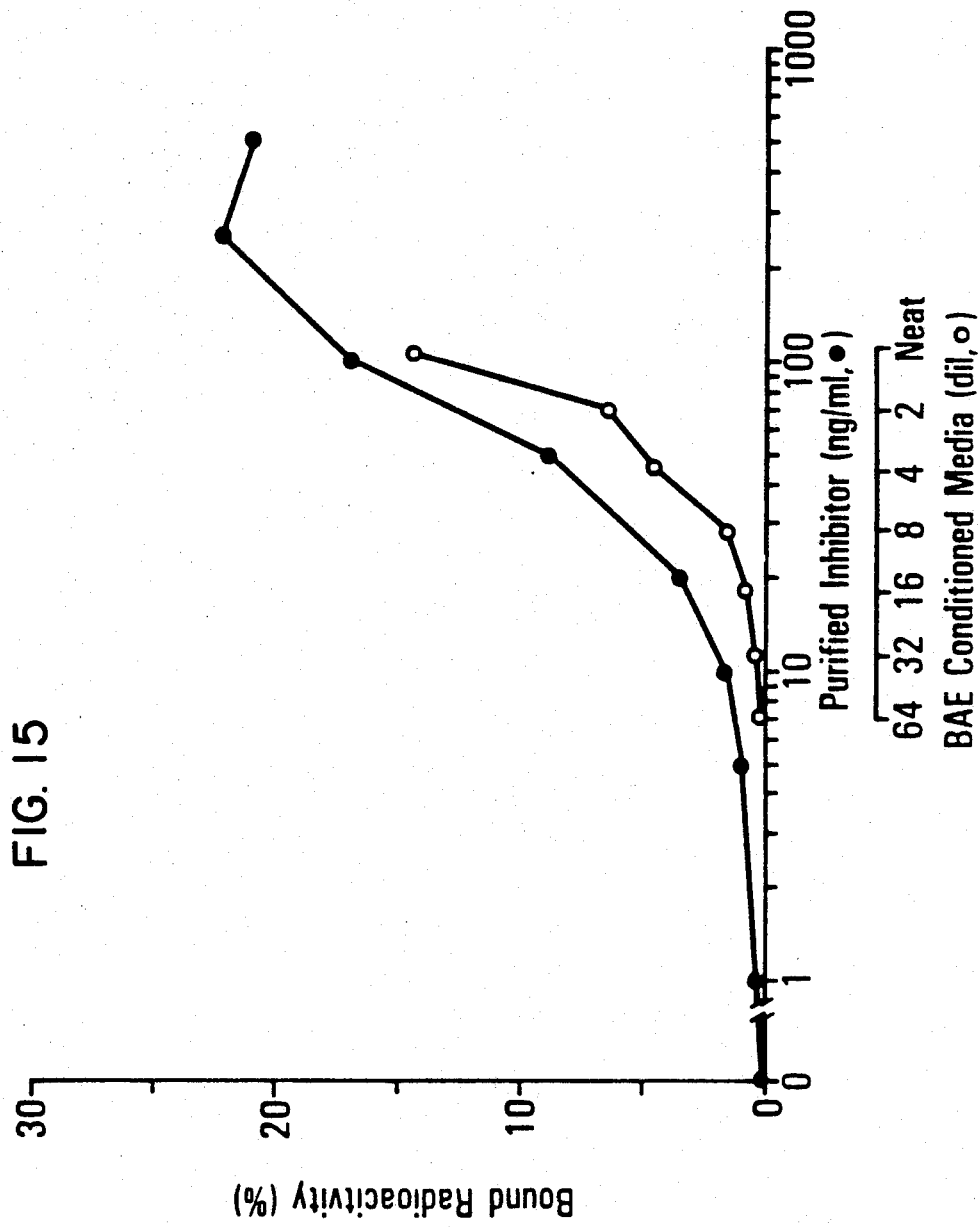

FIG. 15 is a graph illustrating the dose-response curve for the detection of purified inhibitor and inhibitor present in BAE conditioned media, employing the inhibitor binding assay under the particularly preferred conditions established by FIGS. 10-14. t-PA coated wells were incubated for 1 hour at 37° C. with the indicated concentrations of either purified inhibitor (●) or sequential dilutions of bovine aortic endothelial cell (BAE) conditioned media (○). The bound inhibitor was quantified with rabbit anti-inhibitor receptor (1:75) followed by $^{125}$I-goat anti-rabbit IgG ($2.5 \times 10^4$ cpm) as described for FIG. 10.

Figure 16:
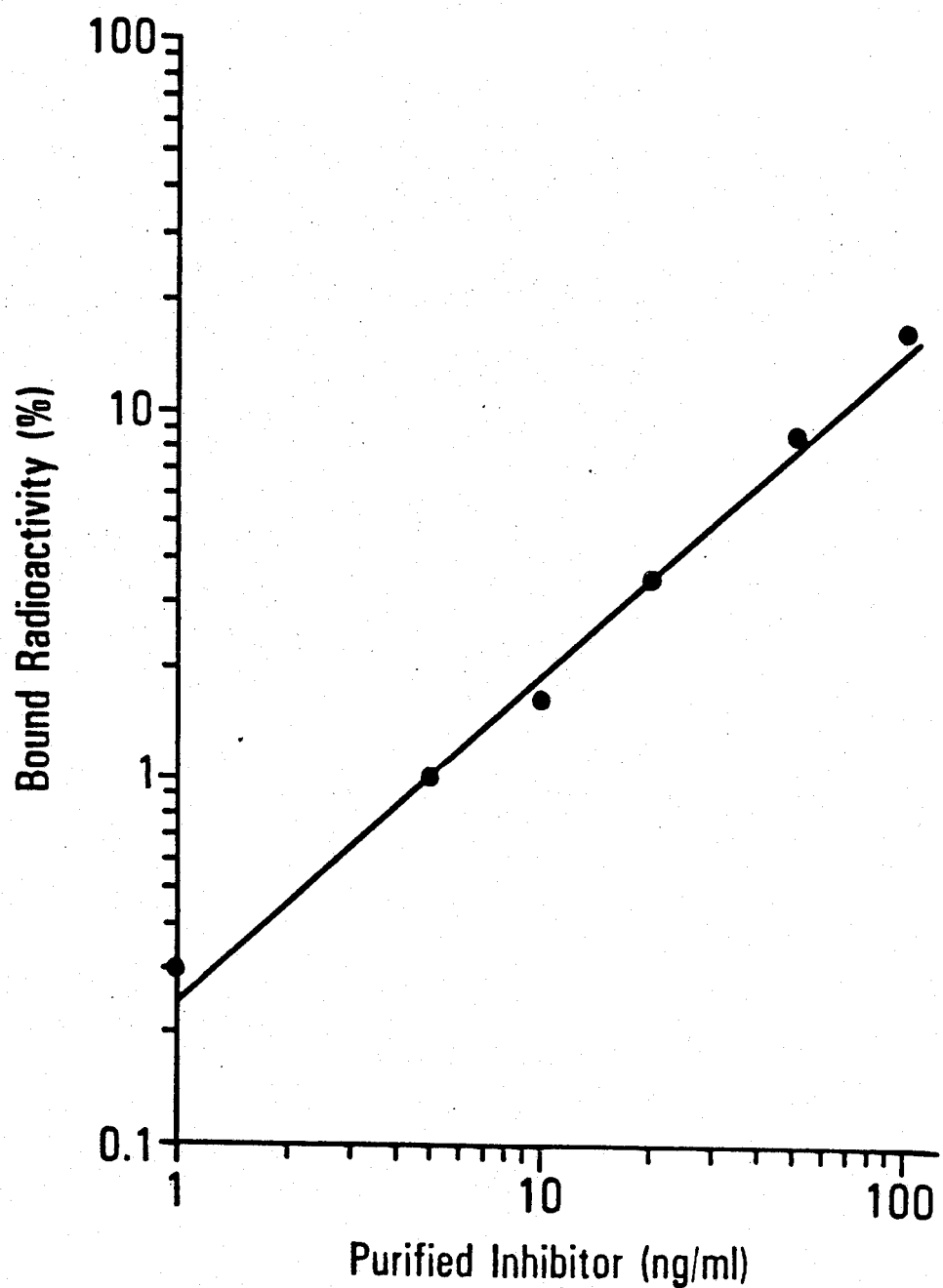

FIG. 16 is a graph illustrating the standard dose-response curve to purified inhibitor of FIG. 15 as represented on a log versus log plot. The binding data for the purified inhibitor shown in FIG. 15 were used.

Figure 17:
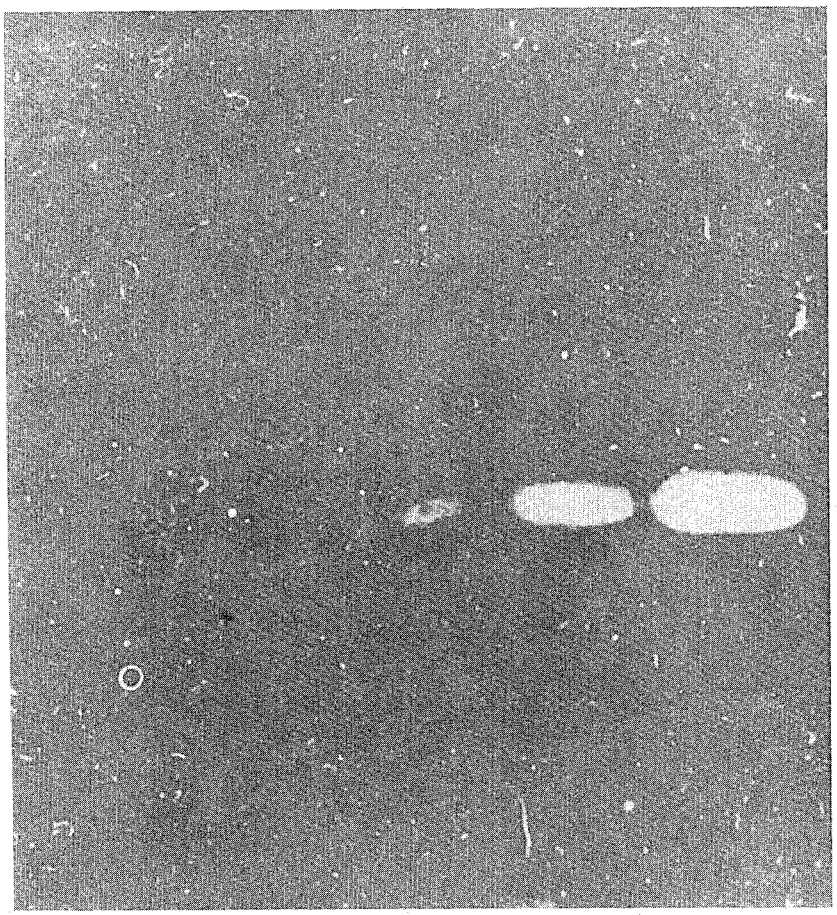

FIG. 17 is a copy of an autogram showing the dose-response curve of inhibitor as detected by reverse fibrin autography. Various concentrations of purified inhibitor were analyzed by SDS-PAGE and reverse fibrin autography as described in detail hereinafter. Lane 1, 0.5 ng; lane 2, 1 ng; lane 3, 2.5 ng; lane 4, 5 ng; lane 5, 10 ng. Molecular weight markers are indicated.

Figure 18:
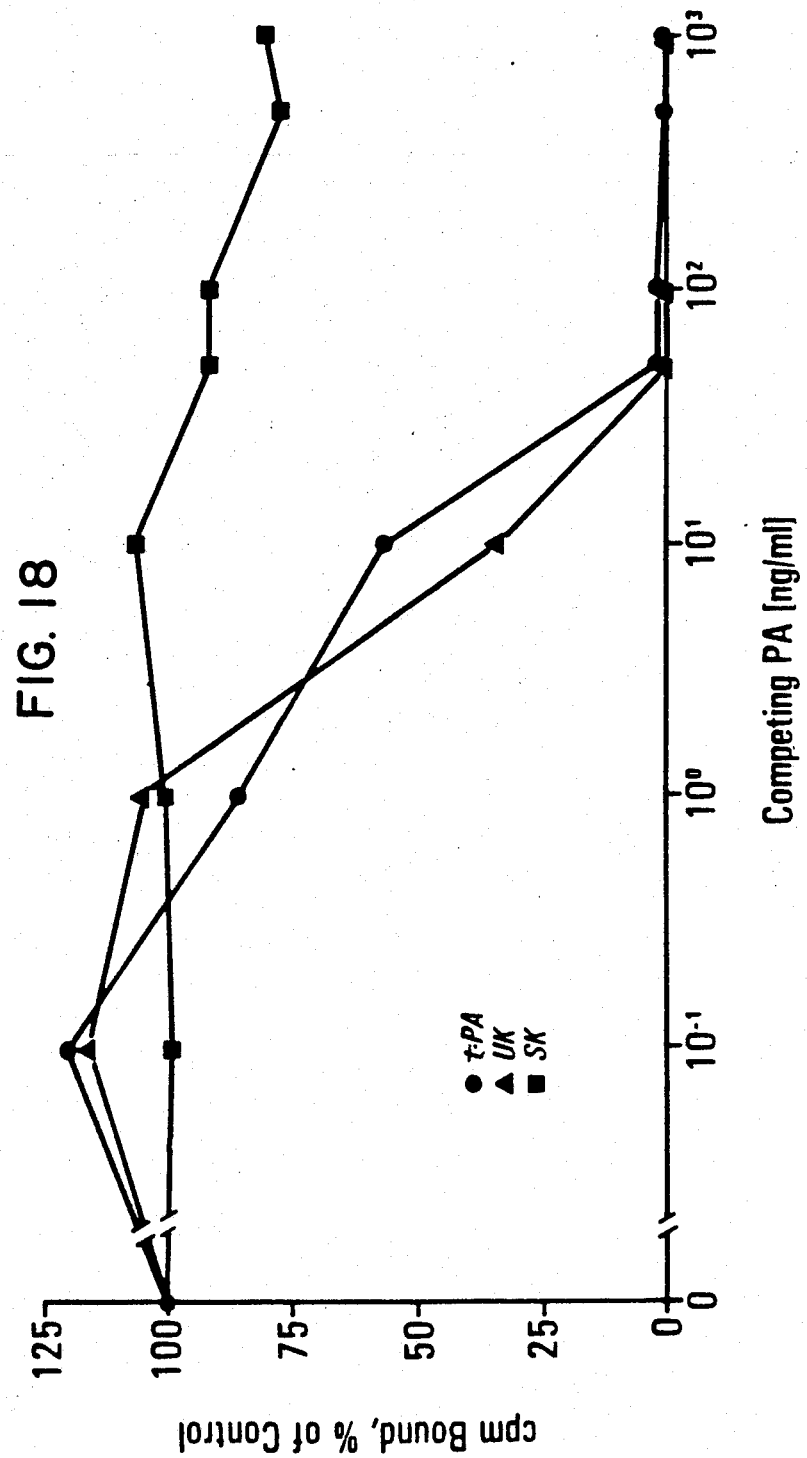

FIG. 18 is a graph illustrating the effect of exogenous PA on the binding of inhibitor to immobilized t-PA. Purified inhibitor (50 ng/ml) was incubated for 1 hour at 37° C. with the indicated concentrations of t-PA (●), u-PA (UK, ▲) or streptokinase (SK, ■). The binding of inhibitor to t-PA was quantified in the inhibitor binding assay described in detail hereinafter.

Figure 19:
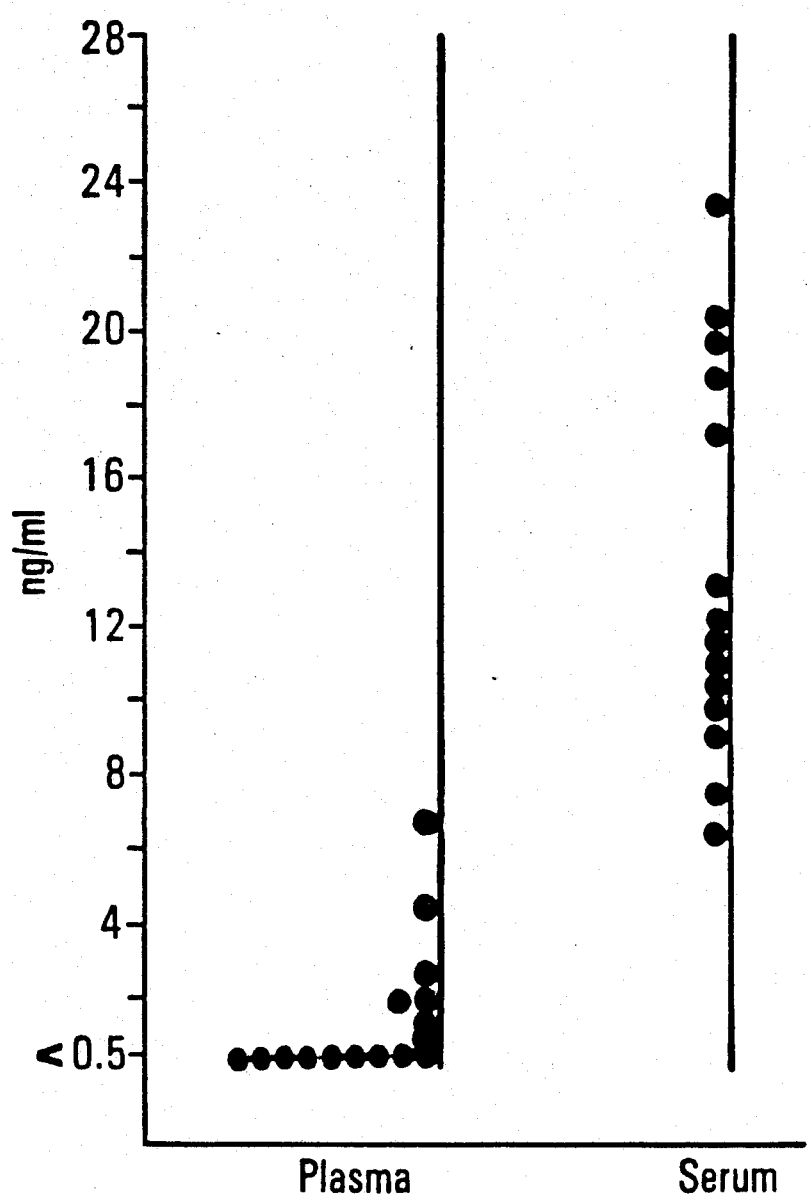

FIG. 19 is a graph illustrating the inhibitor activity in ng/ml of normal human plasma and serum. Blood samples collected by venipuncture from healthy donors were placed into acid-citrated dextrose (ACD). Plasma and serum were prepared from each blood sample, and the inhibitor activity was measured in the inhibitor binding assay described in detail hereinafter.

DETAILED DESCRIPTION OF THE INVENTION

The present invention is directed to a biochemical reagent system and to methods of preparing and using same, as well as to diagnostics utilizing the reagent system. The reagent system comprises (a) a receptor raised in an animal host to a plasminogen activator inhibitor, and (b) an indicating means.

I. GENERAL DISCUSSION

The term "plasminogen activator inhibitor" as used herein is meant to indicate a protein that inhibits or checks the action of a plasminogen activator. "Plasminogen activator" is a protein that activates plasminogen present in blood, particularly in plasma, and converts it into plasmin in the fibrinolytic system of blood clotting. Plasminogen activators useful in the present invention include tissue-type plasminogen activator (t-PA) and urokinase-type plasminogen activator (u-PA). As used herein, "urokinase-type" is meant to indicate urokinase and its homologous proteins as found in mammals other than humans.

The term "receptor" as used herein is meant to indicate a biologically active molecule that binds to an antigen ligand. A receptor molecule of the present invention is an antibody, a substantially intact antibody in substantially purified form, such as is found in ascites fluid or serum of an immunized animal, or an idiotype-containing polypeptide portion of an antibody such as Fab and F(ab')$_2$ antibody portions as are described hereinafter.

Biological activity of a receptor molecule is evidenced by the binding of the receptor to its antigenic ligand upon their admixture in an aqueous medium, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polypeptide portions (antibody combining sites) of antibodies are those portions of antibody molecules that include the idiotype and bind to the ligand, and include the Fab, Fab' and F(ab')$_2$ portions of the antibodies. Fab and F(ab')$_2$ portions of antibodies are well known in the art, and are prepared by the reaction of papain and pepsin, respectively, on substantially intact antibodies by methods that are well known. See for example, U.S. Pat. No. 4,342,566 to Theofilopolous and Dixon. Fab' portions of antibodies are also well known and are prepared by the reduction of F(ab')$_2$ disulfide bonds as by mercaptoethanol followed by alkylation of the reduced cysteine residues with a reagent such as iodoacetamide. Intact antibodies are preferred receptors, and will be utilized as illustrative of the receptor molecules of this invention.

The receptors useful in the present invention are polyclonal receptors. A "polyclonal receptor" (Pab) is a receptor produced by clones of different antibody-producing cells that produce antibodies to a plurality of epitopes of the immunizing molecule.

Non-human, warm blooded animals usable in the present invention as hosts in which the polyclonal receptors are raised can include poultry (such as a chicken or a pigeon), a member of the ratitae bird group (such as an emu, ostrich, cassowary or moa) or a mammal (such as a dog, cat, monkey, goat, pig, cow, horse, rabbit, guinea pig, rat, hamster or mouse). Preferably, the host animal is a rabbit.

Receptors are utilized along with an indicator labelling means or "indicating group" or a "label". The indicating group or label is utilized in conjunction with the receptor as a means for determining that a specific inhibitor has bound to the receptor.

The terms "indicator labelling means", "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry and constitute a part of this invention only insofar as they are utilized with otherwise novel receptors, methods and/or systems.

The indicator labelling means can be a fluorescent labelling agent that chemically binds to antibodies or antigens without denaturing them to form a fluorochrome (dye) that is a useful immunofluorescent tracer. Suitable fluorescent labelling agents are fluorochromes such as fluorescein isocyanate (FIC), flourescein isothiocyanate (FITC), dimethylaminonaphthalene-S-sulphonyl chloride (DANSC), tetramethylrhodamine isothiocyanate (TRITC), lissamine rhodamine B200 sulphonyl chloride (RB 200 SC) and the like. A description of immunofluorescence analysis techniques is found in DeLuca, "Immunofluorescence Analysis", in *Antibody As A Tool*, Marchalonis et al., Eds., John Wiley & Sons, Ltd., pp. 189–231, (1985), which is incorporated herein by reference.

The indicator labelling means can be linked directly to a receptor of this invention, to a useful antigen such as t-PA or u-PA, or may comprise a separate molecule. It is particularly preferred that the indicator means be a separate molecule such as antibodies that bind to a receptor of this invention. *Staphylococcus aureus* protein A, sometimes referred to herein as protein A, may also be used as a separate molecule indicator or labelling means where an intact or substantially intact antibody receptor of this invention is utilized. In such uses, the protein A itself contains a label such as a radioactive element or a fluorochrome dye, as is discussed hereinafter.

The indicating group may also be a biologically active enzyme, such as horseradish peroxidase (HRP) or glucose oxidase, or the like. Where the principal indicating group is an enzyme such as HRP or glucose oxidase, additional reagents are required to visualize the fact that a receptor-ligand complex has formed. Such additional reagents for HRP include hydrogen peroxide and an oxidation dye precursor such as diaminobenzidine. An additional reagent useful with glucose oxidase is 2,2'azino-di-(3-ethylbenzthiazoline-6-sulfonic acid) (ABTS).

Radioactive elements provide another class of label, and are used herein as exemplary of useful labels. An exemplary radiolabelling agent that may be utilized in the invention is a radioactive element that produces gamma ray emissions. Elements which themselves emit gamma rays, such as $^{124}I$, $^{125}I$, $^{128}I$, $^{131}I$, $^{132}I$, and $^{51}Cr$ represent one class of gamma ray emission-producing radioactive element indicating groups. Particularly preferred is $^{125}I$. Another class of useful indicating groups are those elements such as $^{11}C$, $^{18}F$, $^{15}O$, and $^{13}N$ that themselves emit positrons. The positrons so emitted produce gamma rays upon encounters with electrons present in the analysis medium. Also useful is a beta ray emitter, such as $^{111}$indium.

A radioactive polyclonal receptor can be made by culturing in a medium containing radioactive amino acids, as is well known, as well as by isolating the polyclonal receptor and then labelling the polyclonal receptor with one of the above radioactive elements. Radiolabeling of proteins is well known in the art and will not be discussed further herein.

The present invention also contemplates methods of forming a polyclonal receptor and a biochemical reagent system of the invention.

The method of forming a polyclonal receptor for use in a biochemical reagent system of the present invention comprises administering to an animal host, preferably a mammal (e.g., a rabbit, goat or horse) a plasminogen activator inhibitor in an amount sufficient to induce the production of antibodies to the inhibitor. The resulting antibodies are a receptor for the inhibitor. Antisera containing the antibodies are then collected from the immunized host and the receptor so produced is recovered.

The biochemical reagent system of the invention is formed by combining the receptor formed as described above with an indicating means. Suitable indicating means are those previously described hereinbefore. It is particularly preferred that the indicating means be a separate molecule.

A further embodiment of the invention is a solid phase assay method for detecting the presence and quantity of plasminogen activator inhibitor in a sample to be assayed. The method comprises the steps of: (a) providing a solid matrix on which to assay a sample; (b) affixing on the solid matrix a binding reagent that binds (complexes with) to the inhibitor to form a solid phase support; (c) admixing an aliquot of a liquid sample to be assayed with the solid phase support to form a solid-liquid phase admixture; (d) maintaining the admixture for a predetermined time (typically about 2 to 4 hours) sufficient for the binding reagent to bind to (complex with) inhibitor present in the sample; (e) separating the solid and liquid phases; and (f) determining the presence of inhibitor that bound to (complexed with) the binding reagent.

The presence of the inhibitor that complexed with the binding reagent may be determined in a number of ways. In one preferred embodiment, that determination is made by the steps of (i) admixing an aqueous liquid solution of second binding reagent that binds to the inhibitor bound on the solid support with the solid phase obtained after step (e) above to form a second solid-liquid phase admixture, the second binding reagent complexing with the inhibitor; (ii) maintaining the second solid-liquid admixture for a predetermined time sufficient for the second binding reagent to bind (form a complex) with the inhibitor (typically about 2 to about 4 hours); (iii) separating the solid and liquid phases of the second solid-liquid phase admixture; and (iv) determining the quantity of the second binding reagent that bound to the inhibitor, and thereby determining the quantity of inhibitor.

The amount of second binding agent that binds to or complexes with the inhibitor is typically determined by an indicating means, as described hereinbefore. The indicating means may linked to the second binding reagent so that the second binding agent and indicating means are one molecule. More preferably, the second binding reagent and indicating means are separate molecules.

Thus, where the indicating means is linked to the second binding reagent, the above method for determining the presence of inhibitor complexed with the first-named binding reagent may be carried out using the steps of (i) admixing an aqueous, liquid solution of second binding reagent containing a linked indicating means with the solid phase obtained after step (e) above to form a second solid-liquid phase admixture, the second binding reagent binding to (complexing with) the inhibitor, and the indicating means providing a means of determining the quantity of the second binding reagent that bound to the inhibitor; (ii) maintaining the admixtures for a predetermined time sufficient for the second binding reagent to bind to (complex with) the inhibitor; (iii) separating the solid and liquid phases of the second solid-liquid phase admixture; and (iv) determining the quantity of second binding reagent that bound to the inhibitor.

The indicating means is a separate molecule in particularly preferred practice. In such situations, the bound (complexed) inhibitor may be determined by the steps of (i) admixing a liquid solution of second binding reagent with the solid phase obtained after step (e) above to form a second solid-liquid phase admixture, the second binding reagent binding to (complexing with) the inhibitor; (ii) maintaining the admixture so formed for a predetermined period of time sufficient for the second binding reagent to bind to (complex with) the inhibitor; (iii) separating the solid and liquid phases of the second solid-liquid phase admixture; (iv) admixing a separate molecule indicator labelling means (as discussed hereinbefore) to form a third solid-liquid phase admixture; (v) maintaining the third solid-liquid phase admixture for a predetermined period of time sufficient for the second binding reagent and indicator labelling means to bind (typically about 2 to about 4 hours); (vi) separating the solid and liquid phases of the third solid-liquid phase admixture; and (vii) determining the amount of separate molecule indicator labelling means that bound to the second binding reagent.

Details for the above embodiment are given hereinafter wherein the first binding reagent is t-PA or u-PA, the second binding reagent is rabbit anti-inhibitor antibody and the separate molecule indicator means is a goat anti-rabbit IgG antibody.

In yet another method, the amount of inhibitor reacted or complexed with the first binding reagent may be determined without the use of a second binding reagent. In this embodiment, the indicator labelling means is linked directly to the inhibitor, and the amount of inhibitor is determined by that label.

For example, the proteins present in a sample to be assayed may be radiolabelled with 125-iodine following one of the procedures described hereinafter. After separation of the solid and liquid phases of step (e), hereinbefore, the radiolabelled, but unbound, proteins are removed from the admixture thereby leaving radiolabelled, bound inhibitor on the solid support. The presence and amount of that bound, radiolabelled inhibitor can then be determined using a gamma counter. A similar result can be obtained using a reactive fluorescent molecule as the indicator labelling means such as fluoroscein isocyanate to react with the components of the assayed sample in place of the radioactive element.

Preferred first and second binding reagents include tissue-type and urokinase-type plasminogen activators or the above described receptor of the invention. If the first binding reagent utilized is tissue-type or urokinase-type plasminogen activator, then the second binding reagent is the receptor. Alternatively, if the first binding reagent utilized is the receptor, then the second binding reagent is one of the above plasminogen activators. Thus, the first binding reagent is (a) a plasminogen activator selected from the group consisting of t-PA and u-PA, or (b) a receptor of this invention that binds to the inhibitor, and the second binding reagent is (a) a plasminogen activator selected from the group consisting of t-PA and u-PA, or (b) a receptor of this invention. However, the first and second binding reagents are different.

The separate molecule indicator labelling means is preferably used where the second binding reagent is an intact or substantially intact antibody receptor of this invention that binds to the inhibitor. As such, the separate molecule indicator labelling means is preferably an antibody such as goat anti-rabbit IgG or protein A having a linked indicating group such as a radioisotope, enzyme or fluorochrome dye.

The present invention further contemplates a diagnostic system, that may be in the form of a kit, for detecting the presence and quantity of a plasminogen activator inhibitor in a sample. The kit includes at least one package containing (1) as an active ingredient, an effective amount of the biochemical reagent system of the invention in dry, solution, or dispersion form, and (2) t-PA or u-PA.

The diagnostic system may also include a solid matrix that may be a microtiter strip or plate having a plurality of wells. The t-PA or urokinase present is preferably bound to the solid matrix.

Suitable solid matrices useful in the diagnostic system and method described hereinbefore include 96 well microtiter plates sold under the designation Falcon Microtest III Flexible Assay Plates (Falcon Plastics, Oxnard, Calif.) and microtiter strips sold under the designation Immulon I and II (Dynatech, Alexandria, Va.). The microtiter strip or plate is made of a clear plastic material, preferably polyvinyl chloride or polystyrene. Alternative solid matrices for use in the diagnostic system include polystyrene beads, about 1 micron to about 5 millimeters in diameter, available from Abbott Laboratories, North Chicago, Ill.; polystyrene tubes, sticks or paddles of any convenient size; and polystyrene latex whose polystyrene particles are of a size of about 1 micron and can be centrifugally separated from the latex.

The solid matrix may also be made of a variety of materials such as cross-linked dextran, e.g. Sephadex G-25, -50, -100, -200 and the like available from Pharmacia Fine Chemicals of Piscataway, N.J., agarose and cross-linked agarose, e.g. Sepharose 6B, CL6B, 4B, CL4B and the like also available from Pharmacia Fine Chemicals.

The agarose or Sepharose matrices are typically activated for linking using cyanogen bromide. The activated matrix is then washed with one molar glycine and linked to the biochemical reagent system of the invention, t-PA or u-PA without drying of the activated matrix (solid support). The matrix-linked reagent system, t-PA or u-PA is then washed and is ready for use. Further details of use of these solid matrices are provided in Section III, B.

The diagnostic may further include a standard against which to compare the assay results and various buffers in dry or liquid form.

An indicating means such as those described hereinbefore is preferably supplied along with the receptor in the biochemical reagent system of the invention, and may be packaged therewith when linked to the receptor or more preferably is packaged separately when a separate molecule indicating means is used. Additional reagents such as hydrogen peroxide and diaminobenzidine may also be included in the system when an indicating group such as HRP is utilized. Such materials are readily available in commerce, as are many indicating groups, and may not be supplied along with the diagnostic system. In addition, some reagents such as hydrogen peroxide decompose on standing, or are otherwise short-lived like some radioactive elements, and are better supplied by the end-user.

The data from several studies, discussed hereinafter, were performed to assess the nature of the plasminogen activator inhibitor and the ability of the biochemical reagent diagnostic systems of the present invention to detect and quantify plasminogen activator inhibitor bound to plasminogen activator in human serum.

The diagnostic system of the invention is based upon the ability of the inhibitor to bind to t-PA or u-PA immobilized on plastic microtiter wells. After washing, the extent of binding was quantified by admixing and maintaining (incubating) the complex first with rabbit antiserum to the inhibitor and then with $^{125}$I-goat anti-rabbit IgG. Using the diagnostic system and assay method of the present invention, it was found that the reaction between t-PA and the inhibitor was rapid (greater than 78 percent binding within 1 hour), time- and concentration-dependent, and sensitive over a broad range of inhibitor concentrations (1-100 ng/ml). Exogenously added t-PA and u-PA were found to compete with the immobilized t-PA for the inhibitor with a 50 percent reduction in binding obtained with 12 ng/ml of t-PA and 6 ng/ml of u-PA.

It is to be understood that the results discussed hereinbelow are illustrative of embodiments utilizing the biochemical reagent and diagnostic systems of the present invention and the present invention is not intended to be so limited.

II. RESULTS

A. Purification of the Bovine Endothelial Cell (BAE) Inhibitor

It had previously been shown that CM (as described in Section III A, B, hereinafter, and in the following papers) from BAEs contained both tissue-type (t-PA) and urokinase-type (u-PA) plasminogen activators, Levin et al., *J. Cell Biol.*, 94, 631 (1982), as well as an inhibitor of fibrinolysis, Loskutoff et al., *Proc. Natl. Acad. Sci. (U.S.A.)*, 80, 2956 (1983). Fractionation of this CM by affinity chromatography on concanavalin A-Sepharose revealed that the u-PA and t-PAs could be separated from each other, Loskutoff et al., *Blood*, 62, 62 (1983), and suggested that this approach also would be useful for the purification of the inhibitor.

Figure 1:
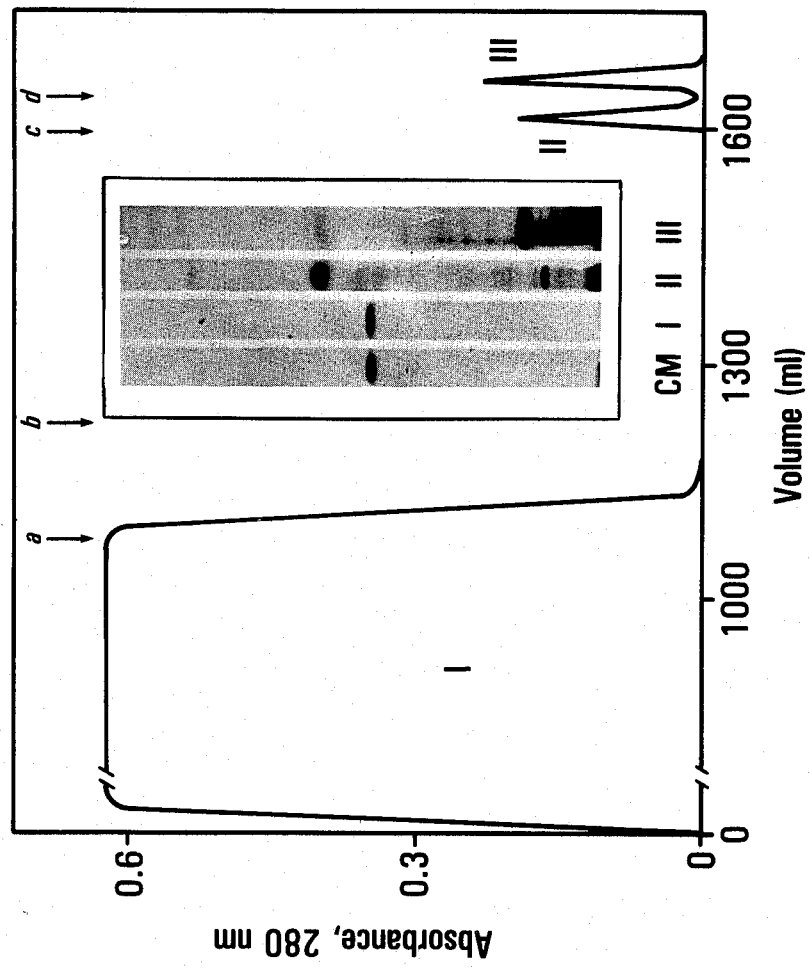
FIG. 1 is a graph illustrating the fractionation of conditioned media (CM) by affinity chromatography on concanavalin A-Sepharose. One liter of CM from confluent bovine aortic endothelial cells (BAEs) was passed over a 10 milliliter (ml) concanavalin A-Sepharose column as described in detail hereinafter. The column was washed sequentially with (a) 1 molar (M) NaCl, (b) 0.001M sodium phosphate, (c) 0.01M sodium phosphate containing 0.5M alpha-methyl-D-mannoside, and (d) 0.01M sodium phosphate containing 0.5M alpha-methyl-D-mannoside and 1M NaCl. The inset shows the protein profile of the starting material (CM), as well as the pooled run-through (I), alpha-methyl mannoside low (II) and high (III) salt fractions, all revealed after sodium dodecyl sulfate-polyacrylamide gel electrophoresis (SDS-PAGE) and staining with Coomassie Brilliant Blue (BioRad, Richmond, Calif.).

One liter of CM was applied to a concanavalin A-Sepharose column and the column was processed as described in Section III hereinafter. The peak fractions were pooled, fractionated by SDS-PAGE, and analyzed for protein by staining with Coomassie Brilliant Blue, and for the presence of fibrinolytic activators and inhibitors by reverse fibrin autography. As shown in FIG. 1, more than 85 percent of the protein applied to the column was recovered in the run-through effluent (pool I). This fraction contained both albumin and u-PA, but no inhibitor (not shown). Some inhibitor was detected in Pool III, the fraction containing the majority of recovered t-PA activity, Loskutoff et al., *Blood*, supra, but represented less than 20 percent of the total inhibitor as judged by the relative size of the lysis-resistance zones, Erickson et al., *Anal. Biochem.*, 137, 454 (1984). The majority of detectable inhibitor activity was recovered in the concanavalin A, pool II fraction, as shown in the inset in FIG. 2, a fraction containing only 5 percent of the total protein. It appeared to comigrate with one of the major stained proteins.

Figure 2:
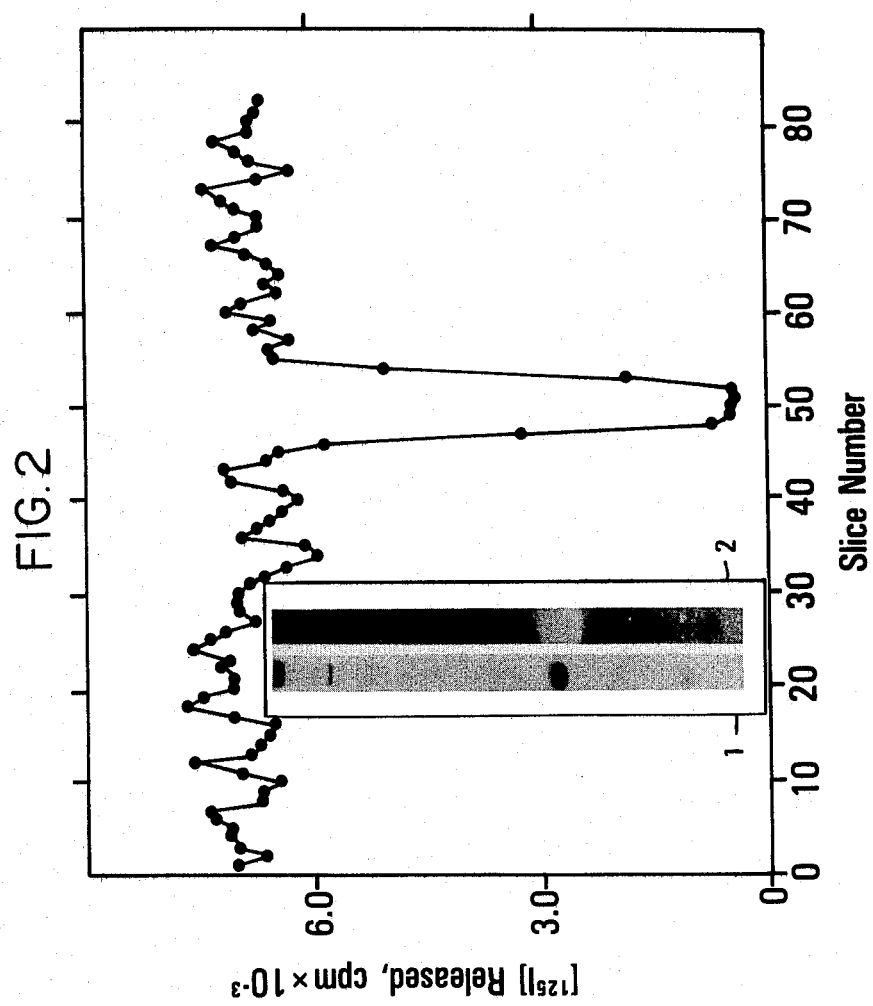
FIG. 2 is a graph illustrating the detection of inhibitor activity of concanavalin A fraction II (above) after SDS-PAGE. The concanavalin A peak II material (FIG. 1) was pooled and fractionated by SDS-PAGE in a tube gel as described in detail hereinafter. The gel was sliced, each slice was eluted into buffer, and then the eluants were tested for their ability to inhibit u-PA-mediated fibrinolytic activity as measured by the $^{125}$I-fibrin plate method (described hereinafter). The inset shows the protein profile (lane 1) and inhibitor activity (lane 2) of similar samples fractionated by SDS-PAGE on slab gels and analyzed by staining with Coomassie Brilliant Blue and by reverse fibrin autography, respectively.

The concanavalin A pool II also was analyzed by SDS-PAGE in tube gels and results are shown in FIG. 2. After electrophoresis, the gel was sliced and extracts of the slices tested for their ability to inhibit u-PA-mediated lysis of $^{125}$I-fibrin. Again, inhibitor activity was detected in a single region of the gel, and migrated with a relative mobility ($R_f$) that was indistinguishable from that of the lysis-resistant zone shown in the inset of FIG. 2 (i.e., $R_f$=0.6). Few other proteins were detected in this region of the gel, suggesting that the purification could be completed by extracting the inhibitor out of such gels.

Figure 3:
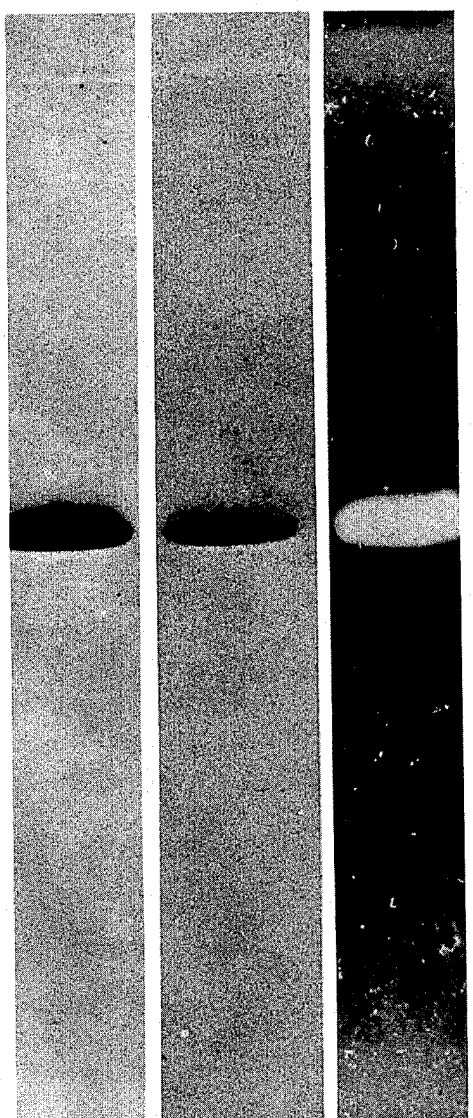
FIG. 3 is a photocopy of a reverse fibrin autogram showing an analysis of purified inhibitor by SDS-PAGE. The gel extracts containing the majority of the inhibitor activity (fractions 49-52 as shown in FIG. 2) were pooled and analyzed on a 7.5-20 percent gradient slab gel as described in detail hereinafter. After electrophoresis, the gel was stained with Coomassie Brilliant Blue (lane 1) and periodic acid-Schiff reagent (lane 2), or tested for inhibitor activity by reverse fibrin autography (lane 3).

The extracts with the highest inhibitor activity (FIG. 2, slices 49–52) were pooled and reanalyzed on 7.5–20 percent gradient gels and the results shown in FIG. 3. A single protein was detected when the gel was stained with Coomassie Brilliant Blue (FIG. 3, lane 1) or periodic acid-Schiff reagent (FIG. 3, lane 2), and it comigrated with the inhibitor as revealed by reverse fibrin autography (FIG. 3, lane 3). The amount of inhibitor antigen present in the starting CM and in the various pooled fractions was determined by the rocket technique of Laurell, *Scand. J. Clin. Lab. Invest*, 29, 21 (1977), using antisera developed to the purified inhibitor (not shown).

These screenings indicated that CM contained 0.6 micrograms/ml of inhibitor, that 600 micrograms of inhibitor were applied to the concanavalin A column (FIG. 1), and that 90 microgams were recovered from the final gel extracts (FIGS. 2 and 3). Thus, this purification protocol yielded a recovery of approximately 15 percent of the starting antigen. The purified inhibitor had an apparent molecular weight ($M_r$) of 50,000±2,500 daltons under both reducing and non-reducing conditions when compared directly to $M_r$ standards (data not shown).

B. Preliminary Characterization of the Purified Inhibitor

Figure 4:
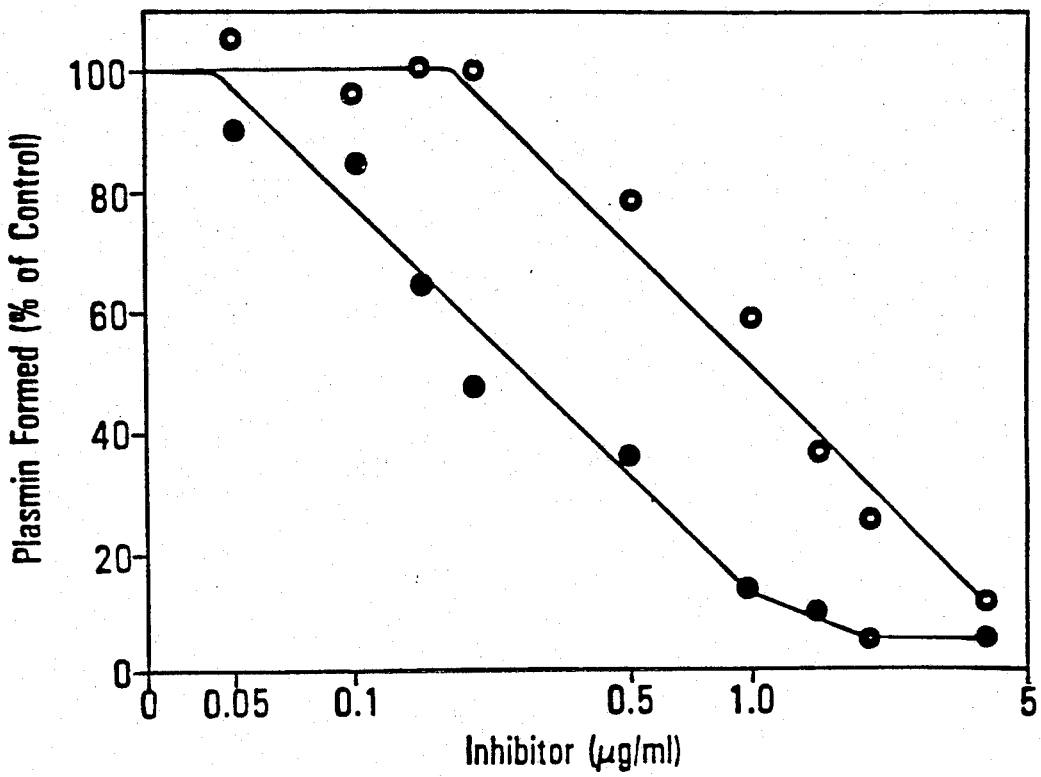
FIG. 4 is a graph illustrating the inhibition of PA activity by the BAE inhibitor. Increasing amounts of the purified inhibitor were preincubated for 5 minutes at 37° C. with 2.5 units/ml of either human u-PA (o) or t-PA (●).

PAs convert single chain plasminogen into two-chain plasmin by cleavage of a single arginine-valine bond, Summaria et al., *J. Biol. Chem.*, 242, 4279 (1967). This process can be monitored by SDS-PAGE in the presence of reducing agents, Mussoni et al., *Thromb. Res.,* 34, 241 (1984); Summaria et al., *J. Biol. Chem.,* supra; Dano et al., *Biochim. Biophys. Acta,* 566, 138 (1979). To determine whether the inhibitor was an anti-activator, its ability to inhibit this cleavage was assessed and the results shown in FIG. 4. The purified inhibitor blocked the ability of both u-PA and t-PA to cleave $^{125}$I-plasminogen into its characteristic heavy and light chains, and did so in a dose-dependent manner. Inhibition of t-PA was associated with the formation of an enzyme-inhibitor complex that was still apparent after SDS-PAGE as shown in FIG. 5.

The inhibitor activity of the purified molecule, like that detected in CM collected from confluent BAEs, Loskutoff et al., *Proc. Natl. Acad. Sci. (U.S.A.),* supra, was not destroyed upon incubation at pH 2.7 for 60 minutes at 37° C., or upon exposure to SDS as shown in FIG. 6. In contrast, the inhibitor activity of purified protease nexin was abolished by these same treatments. The inhibitor activity of these proteins was not affected by incubation for 30 minutes at 37° C. in the presence of 5 percent 2-mercaptoethanol (not shown).

C. Purification of the Inhibitor from BAEs Cultured in the Presence of L[3,4,5-$^3$H] Leucine Both plasma and serum contain inhibitors of fibrinolysis, Loskutoff, *J. Cell Physiol.,* 96, 361 (1978); Mullertz, in *Progress in Chemical Fibrinolysis and Thrombolysis,* Davidson et al. eds., vol. 3, pp. 213–237, Raven Press, New York (1978); Collen, *Thromb. Haemostas.,* 43, 77 (1980). Cultured endothelial cells may internalize or bind these serum proteins and subsequently release them back to the serum-free medium, Cohen, *J. Clin. Invest.,* 52, 2793 (1973); Pastan et al., *Cell,* 12, 609 (1977); Rohrlich et al., *J. Cell Physiol.,* 109, 1 (1981); McPherson et al., *J. Biol. Chem.,* 256, 11330 (1981), during the preparation of CM. To determine whether the inhibitor actually was synthesized by BAEs, or was simply a contaminating serum inhibitor, the inhibitor was purified from the CM of cells cultured in the presence of L[3,4,5-$^3$H] leucine, employing the same protocol as that developed for the purification of the inhibitor from unlabeled CM. Two peaks of radiolabeled proteins were recovered when the concanavalin A-Sepharose column was eluted with alpha-methyl mannoside in the presence of low and high salt (data not shown). The peak II fractions containing inhibitor were pooled and subjected to further analysis by SDS-PAGE and the results shown in FIG. 7. Both inhibitor activity and the majority of the radioactivity were recovered in the same fractions. These two activities also comigrated when the peak inhibitor fractions (fractions 52, 53 in FIG. 7) were pooled, dialyzed, and subjected to subsequent analysis by alkaline PAGE (FIG. 8). Taken together, these data indicated that the inhibitor was a biosynthetic product of the cells, and not a contaminating serum protein.

Immunoprecipitation screenings were performed both to confirm the above results and to quantitate inhibitor synthesis by cloned BAEs. The results are shown in FIG. 9 and in Table I below.

TABLE I

| Cell Isolated[b] | Inhibitor Synthesis by BAEs CPM Recovered[a] | | | |
|---|---|---|---|---|
| | CM | Pool II | Gel Extract | Immunoprecipitate |
| BAE$_{26}$ | 9.3 × 10$^6$ (100%) | 2.9 × 10$^6$ (30%) | 1.2 × 10$^6$ (12%) | — |
| Clone A | 3.2 × 10$^7$ (100%) | — | — | 8.2 × 10$^5$ (2.5%) |
| Clone B | 4.5 × 10$^7$ (100%) | — | — | 1.5 × 10$^6$ (3.4%) |

[a]The total, TCA-precipitable radioactivity in the various fractions and in the immunoprecipitates was determined by standard procedures well known in the art. The data are normalized to the percent (shown in the parenthesis) of the cpm in the starting material (CM) recovered at each step.
[b]In each case, approximately 1.5 × 10$^7$ cells were labeled with L[3,4,5-$^3$H] leucine (20 Ci/ml) for 24 hours as described in Section III hereinafter. The serum-free CM (15 ml) was collected and fractionated as indicated.

In these screenings, radiolabeled CM collected from cloned BAEs was incubated with antibody to the purified inhibitor. The bound material was extracted from the antibody protein A-Sepharose beads, fractionated by SDS-PAGE, and analyzed by autoradiography (FIG. 9). A single radiolabeled polypeptide of an approximate $M_r$ of 50,000 daltons was revealed, and it had inhibitor activity when analyzed by reverse fibrin autography (not shown). This protein did not adsorb to protein A-Sepharose beads prepared with preimmune serum (not shown). The total radioactivity recovered from the various CMs analyzed in these immunoprecipitation screenings, and the recovery of radiolabeled protein at each step of the purification (FIGS. 7–8; Table I), indicates that the inhibitor accounts for between 2.5–12 percent of the total protein synthesized and secreted by the cells in a 24 hour period (Table I).

D. Development and Evaluation of a Functional Assay for Inhibitor (Inhibitor Binding Assay)

Polyvinyl chloride (PVC) plastic wells were coated overnight at 4° C. with varying concentrations of t-PA to determine the optimal concentrations of t-PA for the assay of the present invention as shown in FIG. 10. The wells were washed, blocked with BSA and incubated for 2 hours at 37° C. with three different concentrations of purified inhibitor (20, 50 and 100 ng/ml). After washing, the extent of binding was quantified by incubating the complex first with rabbit anti-inhibitor receptor (diluted 1:100) followed by $^{125}$I-goat anti-rabbit IgG (1.5 × 10$^5$ cpm/well). As the t-PA concentration used to coat the PVC wells was increased from 0.1 to 1.0 microgram/ml, the detection of bound inhibitor increased at all three concentrations (FIG. 10). Increasing the t-PA coating concentration above 1 microgram/ml did not increase the detection of bound inhibitor. Thus, subsequent screenings employed a t-PA concentration of 1 microgram/ml for coating the PVC wells.

The kinetics of the interaction of the inhibitor with immobilized t-PA were determined in order to optimize the incubation period for inhibitor containing solutions. Purified inhibitor (100 ng/ml) was incubated at 37° C. for various times on either t-PA or BSA coated wells. The bound inhibitor was then quantified with the rabbit anti-inhibitor receptor (1:100) followed by $^{125}$I-goat anti-rabbit IgG (1.5 × 10$^5$ cpm/well). The reaction between the inhibitor and immobilized t-PA was a fast reaction with over 75 percent binding occurring within 30 minutes (FIG. 11). During this period, the inhibitor did not bind to control, BSA coated wells. For convenience, a 1 hour incubation time for inhibitor containing solutions was used in subsequent screenings.

The incubation time for the polyclonal receptor and indicating means were similarly optimized. t-PA- or BSA-coated wells were incubated for 1 hour at 37° C. with the inhibitor (50 ng/ml) and then incubated with the rabbit anti-inhibitor receptor for various periods of time. Bound receptor was detected by a 2 hour incubation with the indicator ($^{125}$I-goat anti-rabbit IgG). Alternatively, the wells were incubated for 2 hours with the receptor and the incubation time for the indicator was varied. Both the receptor and indicator associated rapidly with their respective antigen in the assay with over 80 percent binding occurring after 1.5-2 hours (FIG. 12). Therefore, subsequent screenings employed a 2 hour incubation period for both the receptor and indicator.

The effect of varying dilutions of rabbit anti-inhibitor receptor on the detection of innibitor was determined to optimize the assay's sensitivity. t-PA coated wells were incubated for 1 hour at 37° C. with various concentrations of inhibitor (1–100 ng/ml). After washing, the wells were incubated with various dilutions of rabbit anti-inhibitor receptor (1:50–1:500) and the bound antibody was detected with $^{125}$I-goat anti-rabbit IgG ($1.5 \times 10^5$ cpm/ml). Optimal detection of inhibitor occurred at a 1:50–1:75 dilution of the antisera (FIG. 13). Subsequent screenings employed a 1:75 dilution of the antisera. The effect of varying concentrations of $^{125}$I-goat anti-rabbit IgG ($2.5 \times 10^4$–$3 \times 10^5$ cpm/well) was similarly screened to optimize the assays's sensitivity. Optimal detection of inhibitor occurred at $2.5$–$5 \times 10^4$ cpm/well of $^{125}$I-goat anti-rabbit IgG (FIG. 14).

A typical standard dose-response curve of purified inhibitor as detected in this assay is shown in FIG. 15. The assay was sensitive to 1 ng/ml, demonstrated a linear response to inhibitor between 10 and 100 ng/ml and saturated at inhibitor concentrations above 250 ng/ml. A dose-response using bovine aortic endothelial cell conditioned media (CM) is also shown in FIG. 15. Comparison of this curve with the standard curve indicates that this CM sample contained approximately 100 ng/ml of functionally active inhibitor. For convenience, the standard curve was routinely plotted on a log vs. log plot for the purpose of calculating inhibitor concentrations in unknown samples (FIG. 16). It can be seen that plotting in this way gave a straight line.

E. Comparison of the Inhibitor Binding Assay to Reverse Fibrin Autography

The sensitivity of the functional assay (inhibitor binding assay) of tne present invention was compared with the sensitivity of another assay, reverse fibrin autography, commonly used for the detection and quantitation of PA inhibitor. Various concentrations of inhibitor (0.5 ng–10 ng/lane) were fractionated by SDS-PAGE and then analyzed by reverse fibrin autography. The results are shown in FIG. 17. In this technique, the washed polyacrylamide gel was layed on an indicator gel containing fibrin, plasminogen and a PA. Plasmin was slowly formed, resulting in the general lysis of the gel except in areas where inhibitors were present in the corresponding polyacrylamide gel. The sensitivity of reverse fibrin autography was 2.5 ng/lane (FIG. 17) and since 0.1 ml was applied to each lane, its sensitivity was 25 ng/ml, or 25 times less sensitive than the inhibitor binding assay.

F. Applications of the Inhibitor Binding Assay

The inhibitor binding assay of the present invention was used to study the interaction of purified enzymes with the inhibitor. Three purified PAs (t-PA, u-PA and streptokinase) were preincubated for 1 hour at 37° C. with the purified inhibitor (50 ng/ml) and the ability of the inhibitor to subsequently bind to t-PA was quantitated in the inhibitor binding assay. Exogenously added t-PA and u-PA were found to compete with the immobilized t-PA for binding to the inhibitor, with a 50 percent reduction in binding obtained at 12 ng/ml of t-PA and 6 ng/ml of u-PA, as shown in FIG. 18. Neither streptokinase, nor DFP-inactivated t-PA (data not shown) affected the binding of the inhibitor to immobilized t-PA.

The inhibitor binding assay of the invention was also used to detect inhibitor in human plasma and serum. Plasma and serum were prepared from blood collected from 16 healthy human donors and the inhibitor activity in each sample measured in the inhibitor binding assay. Normal human plasma contained low or undetectable levels of inhibitor, as shown in FIG. 19. In contrast, serum from these donors contained high levels of inhibitor activity, as also shown in FIG. 19.

Finally, the assay was employed to determine and compare inhibitor levels in plasma from normal donors and donors with suspected abnormalities in their hemostatic system. The results are shown below in Table II.

TABLE II

Detection of Inhibitor in Normal and Patient Plasma

| Sample | Dilution | cpm Bound | Inhibitor (ng/ml) |
|---|---|---|---|
| Normal plasma | 1:5 | 1500 | N.D.[1] |
|  | 1:10 | 700 | N.D. |
| Patient Plasma | 1:5 | 4700 | 25 |
|  | 1:10 | 2300 | 25 |

[1]"N.D." indicates no inhibitor detected (less than 2 ng/ml).

These samples were kindly provided by Dr. B. Wiman. It can be seen from this screening that no inhibitor was detected in normal plasma, while the patient had approximately 25 ng/ml. This same patient was shown to have elevated inhibitor when studied with a different assay in Wiman, *Thrombosis Research*, 31, 427 (1983).

III. MATERIALS AND METHODS

A. Plasminogen Activator

Tissue-type plasminogen activator (t-PA) was isolated from human melanoma cell conditioned media as described in Rijken et al., *J. Biol. Chem.*, 256, 7035 (1981). Briefly, human melanoma cells were grown to confluent monolayers in plastic tissue culture flasks (Falcon, Oxnard, Calif.) at 37° C. in atmospheric air supplemented with 6 percent of $CO_2$. The growth medium consisted of 100 ml of modified Eagle's essential medium supplemented with sodium bicarbonate (16 ml of a 7.5 percent solution per liter of medium), L-glutamine (10 ml of a 200 mM solution per liter of medium), and heat-inactivated newborn calf serum (final concentration, 10 percent). The cells were washed with medium without calf serum and incubated with 25 ml of serum-free medium. The resulting conditioned medium (CM) was harvested and replaced on 3 consecutive days, centrifuged at 7000 x g for 30 minutes and stored at $-20°$ C. until use. When indicated, Aprotinin (Calbiochem-Behring, La Jolla, Calif.) was added, both to the serum-containino and to the serum free medium (20 KIU/ml, final concentration).

Commercially available urokinase (5×10⁵ CTA units of WINKINASE, Sterling-Winthrop, Rensselaer, N.Y.) was purified further by affinity chromatography as described in Holmberg et al., *Biochim. Biophys. Acta*, 445, 215 (1976).

B. Plasminogen Activator Inhibitor

Bovine aortic endothelial cells (BAEs) employed for the purification of the inhibitor were isolated from the aorta of cows by the method of Booyse et al., *Thromb. Diathes. Haemorrh.*, 34, 825 (1975), whose teachings are incorporated herein by reference, and cultured in 150 cm² flasks (Falcon Plastics, Oxnard, Calif.) in 15 ml of modified Eagle's medium supplemented with 10 percent fetal calf serum (Irvine Scientific, Santa Ana, Calif.) as described in Levin et al., *Thromb. Res.*, 15, 869 (1979). The cells for the screenings had been passaged 16-22 times at a 1:5 ratio, and in general had been confluent for at least one week prior to the preparation of conditioned media (CM) as described below.

Cloned BAEs were employed for some of the metabolic labelling screenings. These clones were developed from single cells that grew out of a primary cell preparation. Briefly, freshly isolated cells were seeded into 60 mm dishes and allowed to attach overnight. The cells were washed with pre-warmed medium, released from the culture dish with trypsin (GIBCO, Long Island, N.Y.), dispersed gently with a pipette, and diluted to approximately 20 cells per ml in growth medium. Four to five aliquots (50 microliters each) of the diluted cells were then placed on the inverted sterile underside of Cooper dish lids (Falcon Plastics, Oxnard, Calif.) and incubated for 60 minutes at room temperature to allow cell attachment.

After the position of each of the cellular droplets was marked with a pen, the lids were inverted back onto Cooper dish bottoms containing confluent BAEs in 6.7 ml of growth medium. The confluent BAEs had been maintained in this medium for 24 hours, presumably elaborating growth factors, Gajdusek et al., *J. Cell Biol.*, 85, 467 (1980). The marked areas were examined in the microscope, and those areas containing single cells were monitored on consecutive days for cell growth. When these clones had grown to a few thousand cells, the cells were removed by ring cloning in the presence of trypsin, distributed into 0.5 cm microtiter wells (Falcon) containing 100 microliters of growth medium, and allowed to grow to confluency. Empty lids also were inverted onto Cooper disn bottoms containing confluent BAEs, and served as controls for this method. These lids remained free of cells throughout the incubation period indicating that cells from bottoms did not detach and reattach on the lids. The clones developed by this procedure were positive for Factor VIII-related antigen indicating that they consisted of endothelial cells, Jaffe et al., *J. Clin. Invest.*, 52, 2757 (1973).

Confluent monolayers were then washed twice with 15 ml of PBS and subsequently incubated with 15 ml of serum-free medium. After 24 hours, the resulting CM was collected, pooled, centrifuged for 5 minutes at 400 x g and, after adding $NaN_3$ and Tween 80 (Sigma Chemicals, St. Louis, Mo.) to concentrations of 0.02 percent and 0.01 percent respectively, stored at −30° C. until further use. Approximately 1 liter of CM was passed over a 10 ml concanavalin A-Sepharose (Sigma Chemicals, St. Louis, Mo.) column (1.5×5 cm) previously equilibrated with phosphate-buffered saline (PBS) containing 0.02 percent $NaN_3$ and 0.01 percent Tween 80 [polyoxyethylene (80) sorbitan monooleate], at a speed of 10 ml/h at 4° C.

After collecting the flow-through material, the column was washed with at least 10 column volumes of PBS containing 1M NaCl, 0.01 percent Tween 80 and 0.02 percent $NaN_3$ (pH 7.4) to remove non-specifically adsorbed proteins. The column was washed with approximately the same volume of this buffer but without the added NaCl, and then eluted in 2 steps. In the first, protein was eluted with 0.01M sodium phosphate, pH 7.2, containing 0.5M alpha-methyl-D-mannoside (Sigma Chemicals, St. Louis, Mo.), 0.02 percent $NaN_3$ and 0.01 percent Tween-80, at a speed of 2.5 ml/h. The column was eluted a second time with the same buffer but containing 1M NaCl.

The second step in the purification involved preparative SDS-PAGE. The inhibitor-containing fractions (identified by slab gel electrophoresis and reverse fibrin autography) were pooled and aliquots (225 microliters) were subjected to SDS-PAGE in tube gels. When the tracking dye reached the bottom of the gel, the gels were frozen and cut into 1 mm slices. Every two slices were combined and extracted for 24 hours at 4° C. with 0.2 ml of PBS containing 0.01 percent Tween. Each extract was then tested for inhibitor activity by the $^{125}I$-fibrin plate assay (described below). The fractions containing tne peak of inhibitor activity were pooled and stored at −70° C. until further use.

The inhibitor also was purified from CM collected from cells cultured in the presence of L-[3,4,5-$^3$H] leucine. In this case, the cultures were washed twice with 15 ml of leucine-free MEM (GIBCO, Long Island, N.Y.) and then were incubated in the presence of 15 ml of leucine-free MEM containing 20 microCi/ml of L-[3,4,5-$^3$H] leucine (158 Ci/mmol; New England Nuclear, Boston, Mass.). After 24 hours, the media were collected as described above, combined with 55 ml of unlabeled CM, and passed over a 1 ml concanavalin A-Sepharose column (0.6×3.5 cm) at a speed of 4 ml/h. The column was washed and eluted at 1 ml/h. Again, the inhibitor-containing fractions were pooled and subjected to preparative tube gel electrophoresis. The resulting inhibitor containing gel extracts were stored at −70° C. until further use.

Polyclonal receptors to the purified inhibitor were raised in rabbits as described in detail hereinafter. Protein A-Sepharose CL-4B (Pharmacia Fine Chemicals, Piscataway, N.J.) was rehydrated in PBS containing 0.02 percent $NaN_3$, 0.05 percent Tween 20 [polyoxyethylene (20) sorbitan monolaurate] and 0.1 percent bovine serum albumin, and washed 3 times with a ten-fold excess of this buffer. The IgG fraction of the antisera was coupled to the washed beads as specified by the manufacturer at a ratio of approximately 80 micrograms protein A-Sepharose per 40 microliters of either anti-inhibitor reagent or pre-immune serum. The IgG-coated beads were added to 1 ml of CM collected from cloned BAEs cultured in the presence of [3,4,5-$^3$H] leucine. The samples were incubated for 1 hour at room temperature, the beads were washed by centrifugation (3 times with 1 ml of PBS-Tween buffer) and extracted for 1 hour at 37° C. with 0.25M Tris-HCl (pH 6.8) containing 2.2 percent SDS, 20 percent glycerol, 0.025 percent bromophenol blue and 2.5 percent (v/v) 2-mercaptoethanol. The resulting supernatant was analyzed by SDS-PAGE in slab gels or by liquid scintillation counting.

SDS-PAGE in slab (15×10×0.15 cm) and tube (10×0.5 cm) gels was then performed according to Laemmli, *Nature (Lond.)*, 227, 680 (1970), whose illustrative teachings are incorporated herein by reference. The stacking gel consisted of 4 percent polyacrylamide and the separation gel of 9 percent polyacrylamide (both gels had a cross linkage of 3 percent). Slab gels consisting of a 7.5-20 percent gradient of polyacrylamide in the separation gel also were prepared. After electrophoresis, the gels were fixed and stained either with 50 percent tricholoracetic acid containing 1 percent Coomassie Brilliant Blue (BioRad, Richmond, Calif.), or with periodic acid Schiff reagent, as in Ginsburg et al, in *Methods in Hematology*, Harker et al. eds., vol. 8, pp. 158-176, Churchill Livingstone, N.Y. (1983).

Molecular weight standards employed to determine the apparent molecular weight of the purified inhibitor included phosphorylase B (92,500), human plasminogen (90,000), transferrin (77,000), bovine serum albumin (66,200), human serum albumin (66,000), ovalbumin (43,500), carbonic anhydrase (31,000), soybean trypsin inhibitor (21,500), lysozyme (14,400) and the 66,000, 52,300, and 46,500 subunits of human fibrinogen.

To localize radiolabeled proteins, the stained slab gels were dried and processed for autoradiography as described in Bonner et al., *Eur. J. Biochem.*, 46, 83 (1974). The positions of the radiolabeled protein in tube gels was determined by slicing the gels into 1 mm pieces, extracting each gel slice into buffer as described above, and determining the radioactivity in each fraction.

Alkaline (SDS-free) continuous PAGE was performed as in Hjerten et al., *Anal. Biochem.*, 11, 219 (1965), using 0.37M Tris-glycine (pH 9.5) as both gel- and running buffer. Tube gels were 10 percent polyacrylamide with a cross linkage of 2.5 percent. Samples were brought to 40 percent sucrose, applied to the gel, and subjected to electrophoresis, first for 0.5 hours at 2.5 mA/cm$^2$ and then for 1-1.5 hours at 5 mA/cm$^2$.

Isoelectric focusing gels were prepared in glass tubes (2.5 mm) as in O'Farrell, *J. Biol. Chem.*, 250, 4007 (1975). The resulting pH gradient was determined by cutting the gels into 1 mm slices. Every two slices were combined and extracted into 0.2 ml H$_2$O for 18 hours at 4° C., and the pH and radioactivity in each of these extracts was determined. Slices from parallel gels also were extracted into 0.2 ml PBS/Tween and assayed for inhibitor activity and radioactivity.

Inhibitor activity in polyacrylamide gels was localized either by direct measurement of the ability of the gel extracts to inhibit u-PA-mediated lysis of $^{125}$I-fibrin [fibrin-plate method of Loskutoff et al., *Proc. Natl. Acad. Sci. (U.S.A.)*, 74, 3903 (1977)], or by reverse fibrin autography, as in Erickson et al., *Anal. Biochem.*, 137, 454 (1984). In the latter technique, the white lysis-resistant zones in the indicator film resulted from the presence of inhibitors in the slab gel.

To determine the stability of the inhibitor under denaturing conditions, the purified molecule (20 micrograms/ml) was incubated for 1 hour at 37° C. in 0.02M glycine, pH 2.7, containing 25 micrograms/ml of human serum albumin. The sample was neutralized by the addition of three volumes of assay buffer (pH 8.1) and subsequently tested at various dilutions made in assay buffer for residual activity by the $^{125}$I-fibrin plate assay. Inhibitor (20 micrograms/ml) also was incubated for 1 hour at 37° C. in PBS containing 0.025 percent SDS and albumin (25 micrograms/ml). The SDS was neutralized by the addition of three volumes of assay buffer containing 0.18 percent Triton X-100 [polyoxyethylene (9) octyl phenyl ether], and residual inhibitor activity was measured. Samples treated with PBS instead of glycine and SDS served as controls for these screenings. The effect of acid glycine and SDS on the inhibitor activity of purified protease nexin (160 micrograms/ml) was determined in a similar manner.

C. Formation of Polyclonal Receptors

Antisera to the inhibitor were raised in New Zealand rabbits by subcutaneous injections of 20 micrograms of purified inhibitor dissolved in 1 ml of saline and emulsified with 1 ml of Freund's complete adjuvant (Miles Laboratories, Naperville, Ill.). Booster injections employing 10 micrograms of purified inhibitor in 0.5 ml of saline and emulsified with an equal quantity of incomplete Freund's adjuvant (Miles Laboratories, Naperville, Ill.) were administered at 2 week intervals. Serum containing polyclonal receptors to the inhibitor was collected 10 days after the third and fourth immunizations and pooled.

D. Inhibitor Binding to t-PA Assay

Purified t-PA (50 microliters/well, 1 microgram/ml) in phosphate-buffered saline (PBS) was incubated overnight at 4° C. in U-bottom microtiter plates (PVC plastic, Falcon 3911, Microtest III, Falcon, Oxnard, Calif.). At this and every subsequent step, the plates were washed with SPRIA buffer (PBS supplemented with 0.1 percent BSA, 0.05 percent NaN$_3$ and 0.05 percent Tween 20). To "block" any remaining sites on the plastic, 3 percent BSA (200 microliters/well) was incubated in the wells for 1 hour at 37° C. Test samples and standard curves of purified inhibitor were prepared in dilution buffer (PBS supplemented with 3 percent BSA, 5 mM EDTA, 0.1 percent Tween 80, and 0.02 percent NaN$_3$) and 50 microliters/well were incubated for 1 hour at 37° C. Bound inhibitor was detected by incubation for 2 hours 37° C. with rabbit anti-inhibitor receptor (1:75 dilution in dilution buffer, 50 microliters/well). The bound antibody-inhibitor-t-PA complex then was quantitated by incubation for 2 hours at 37° C. with $^{125}$I-labeled goat anti-rabbit IgG (5×10$^4$ cpm/well, Cappel Laboratories, Cochranville, Pa.). The wells were cut individually and the radioactivity in each well determined in a gamma counter (CT (80-800) CT/T, General Electric, Milwaukee, Wisc.).

E. Miscellaneous

Plasminogen was purified from outdated human plasma by affinity chromatography on lysine-Sepharose as described in Deutsch et al., *Science*, 170, 1095 (1970). Protein was determined by the method of Bradford, *Anal. Biochem.*, 12; 248 (1976), using bovine serum albumin as the standard. PA activity was assayed on $^{125}$I-fibrin coated multiwell tissue culture dishes as described by Loskutoff et al., *Proc. Nat. Acad. Sci. (U.S.A.)*, 74, 3903 (1977). Proteins were enzymatically labeled with $^{125}$I using solid-state lactoperoxidase/glucose oxidase reagents (Bio-Rad Laboratories, Richmond, Calif.) and carrier-free Na $^{125}$I (Amersham, Arlington Heights, Ill.), or, alternatively by the Iodo-gen procedure of Fraker et al., *Biochem. Biophys. Res. Commun.*, 80, 849 (1978), modified so that the labeling interval was only 5 minutes and the temperature was 4° C. A typical specific activity of the final product was 1-4×10$^6$ cpm/microgram protein. Bovine fibrinogen (fraction II, Calbiochem-Behring, La Jolla, Calif.) was purified as suggested in Mosesson, *Biochim. Biophys. Acta*, 57, 204 (1962) to remove plasminogen. Protease nexin was purified from cultured human fibroblasts as in Scott et al., *J.*

Biol. Chem., 258, 10439 (1983) and kindly provided by Dr. J. Baker, University of Kansas, Lawrence, Kans. The $^{125}$I-pilasminogen cleavage assay was performed as described in Loskutoff et al., J. Biol. Chem., 256, 4142 (1981) and Mussoni et al., Thromb. Res., 34, 241 (1984).

The foregoing is intended as illustrative of the present invention but not limiting. Numerous variations and modifications may be effected without departing from the true spirit and scope of the invention.

What is claimed:

1. A diagnostic kit for detecting the presence and quantity of an endothelial cell plasminogen activator inhibitor in a sample, said kit comprising at least one package that contains:
   (1) as an effective amount of a biochemical reagent system comprised of (a) receptor protein that can bind to said inhibitor and (b) an indicating group, wherein said reagent system binds selectively with a specific plasminogen activator inhibitor that binds to and inhibits a plasminogen activator, and
   (2) a plasminogen activator selected from the group consisting of tissue-type plasminogen activator and urokinase-type plasminogen activator that can bind to plasminogen activator inhibitor.

2. The diagnostic kit of claim 1 wherein said plasminogen acitvator is bound to a solid matrix.

3. The diagnostic kit of claim 1 wherein said indicating group is a separate molecule from said receptor and is packaged separately from said receptor.

4. A solid phase assay method for detecting the presence and quantity of an endothelial cell plasminogen activator inhibitor, in a sample to be assayed, comprising he steps of:
   (a) providing a solid matrix on which to assay said sample;
   (b) affixing on said solid matrix a binding reagent that binds to said inhibitor to form a solid phase support, said binding reagent being either (i) a polyclonal receptor to said inhibitor, or (ii) a plasminogen activator selected from the group consisting of tissue-type plasminogen activator and urokinase-type plasminogen activator;
   (c) admixing an aliquot of a liquid sample to be assayed with said solid phase support to form a solid-liquid phase admixture;
   (d) maintaining said admixture for a predetermined time sufficient for said binding reagent to bind to said inhibitor present in said sample to form a solid phase-bound inhibitor-reagent complex;
   (e) separating said solid and liquid phases;
   (f) admixing an aqueous liquid solution of a second binding reagent that binds to said inhibitor portion of said inhibitor-reagent complex bound on said solid support to form a second solid-liquid phase admixture, said second binding reagent being the other of the two of said first binding reagents not used in step (b);
   (g) maintaining said second solid-liquid phase admixture for a predetermined time sufficient for said second binding reagent to bind to said inhibitor present in said complex;
   (h) separating the solid and liquid phases of said second solid-liquid phase admixture; and
   (i) determining the quantity of said second binding reagent that bound to said inhibitor and thereby determining the quantity of inhibitor.

5. The method of claim 4, wherein the quantity of said second binding reagent that bound to said inhibitor is determined by an indicating means.

6. The method of claim 5, wherein said second binding reagent and said indicating means are separate molecules.

7. The method of claim 4 wherein said second binding reagent is linked to said indicating means.

8. The method of claim 4, wherein the determination of step (i) is carried out by the additional steps of:
   admixing a second aqueous, liquid solution containing a separate molecular indicator labelling means with the separated solid phase obtained in step (h) to form a third solid-liquid phase admixture;
   maintaining said third solid-liquid phase admixture for a predetermined time sufficient for said indicator labelling means to bind to said second binding reagent;
   separating the solid and liquid phases of said third solid-liquid phase admixture; and
   determining the quantity of separate molecule indicator labelling means bound to said second binding reagent.

9. The method of claim 8 wherein said first binding reagent is a plaasminogen activator selected from the group consisting of tissue-type plasiminogen acitvator and urokinase-type plasminogen activator.

10. The method of claim 8 wherein said second binding reagent is rabbit anti-inhibitor antibody.

11. The method of claim 8 wherein said separate molecule indicator means is an $^{125}$I-goat anti-rabbit IgG antibody.

12. A solid phase assay method for detecting the presence and quantity of an endothelial cell plasminogoen activator inhibitor in a sample to be assayed comprising the steps of:
   (a) providing a solid matrix on which to assay said sample;
   (b) affixing on said solid matrix a binding reagent that binds to said inhibitor to form a solid phase support, said binding reagent being selected from the group consisting of tissue-type plasminogen activator and urokinase-type plasminogen activator;
   (c) admixing an aliquot of a liquid sample to be assayed with said solid phase support to form a solid-liquid phase admixture;
   (d) maintaining said admixture for a predetermined time sufficient for said binding reagent to bind to inhibitor present in said sample;
   (e) separating said solid and liquid phases;
   (f) admixing an aqueous liquid solution of a second binding reagent that binds to said inhibitor bound on said solid support with said separated solid phase, said second binding reagent being a receptor for said inhibitor;
   (g) maintaining said solid-liquid admixture for a predetermined time sufficient for said second binding reagent to bind to said inhibitor;
   (h) separating the solid and liquid phases of said second solid-liquid phase admixture; and
   (i) determining the quantity of said second binding reagent that bound to said inhibitor and thereby determining the quantity of inhibitor.

13. A solid phase assay method for detecting the presence and quantity of an endothelial cell plasminogen activator inhibitor, in a sample to be assayed, comprising the steps of:

(a) providing a solid matrix on which to assay said sample;

(b) affixing on said solid matrix a polyclonal receptor that binds to said inhibitor to form a solid phase support;

(c) admixing an aliquot of a liquid sample to be assayed with said solid phase support to form a solid-liquid phase admixture;

(d) maintaining said admixture for a predetermined time sufficient for said polyclonal receptor to bind to said inhibitor present in said sample to form a solid phase-bound inhibitor-reagent complex;

(e) separating said solid and liquid phases;

(f) admixing an aqueous liquid solution of tissue-type plasminogen activator that binds to said inhibitor portion of said inhibitor-reagent complex on said solid support to form a second solid-liquid phase admixture;

(g) maintaining said second solid-liquid phase admixture for a predetermined time sufficient for said tissue-type plasminogen activator to bind to said inhibitor present in said complex;

(h) separating the solid and liquid phases of said second solid-liquid phase admixture; and (i) determining the quantity of said tissue-type plasminogen activator that bound to said inhibitor and thereby determining the quantity of inhibitor.

14. A solid phase assay method for detecting the presence and quantity of an endothelial cell plasminogen activator inhibitor, in a sample to be assayed, comprising the steps of:

(a) providing a solid matrix on which to assay said sample;

(b) affixing on said solid matrix a polyclonal receptor that binds to said inhibitor to form a solid phase support;

(c) admixing an aliquot of a liquid sample to be assayed with said solid phase support to form a solid-liquid phase admixture;

(d) maintaining said admixture for a predetermined time sufficient for said polyclonal receptor to bind to said inhibitor present in said sample, to form a solid phase-bound inhibitor-reagent complex;

(e) separating said solid and liquid phases;

(f) admixing an aqueous liquid solution of a urokinase-type plasminogen activator that binds to said inhibitor portion of said inhibitor-reagent complex bound on said solid support to form a second solid-liquid phase admixture;

(g) maintaining said second solid-liquid phase admixture for a predetermined time sufficient for said urokinase-type plasminogen activator to bind to said inhibitor present in said complex;

(h) separating the solid and liquid phases of said second solid-liquid phase admixture; and (i) determining the quantity of said urokinase-type plasminogen activator that bound to said inhibitor and thereby determining the quantity of inhibitor.

15. A solid phase assay method for detecting the presence and quantity of an endothelial cell plasminogen activator inhibitor, in a sample to be assayed, comprising the steps of:

(a) providing a solid matrix on which to assay said sample;

(b) affixing on said solid matrix a tissue-type plasminogen activator that binds to said inhibitor to form a solid phase support;

(c) admixing an aliquot of a liquid sample to be assayed with said solid phase support to form a solid-liquid phase admixture;

(d) maintaining said admixture for a predetermined time sufficient for said tissue-type plasminogen activator to bind to said inhibitor present in said sample, to form a solid phase-bound inhibitor-reagent complex;

(e) separating said solid and liquid phases;

(f) admixing an aqueous liquid solution of a polyclonal receptor that binds to said inhibitor portion of said inhibitor-reagent complex bound on said solid support to form a second solid-liquid phase admixture;

(g) maintaining said second solid-liquid phase admixture for a predetermined time sufficient for said polyclonal receptor to bind to said inhibitor present in said complex;

(h) separating the solid and liquid phases of said second solid-liquid phase admixture; and (i) determining the quantity of said polyclonal receptor that bound to said inhibitor and thereby determining the quantity of inhibitor.

16. A solid phase assay method for detecting the presence and quantity of an endothelial cell plasminogen activator inhibitor, in a sample to be assayed, comprising the steps of:

(a) providing a solid matrix on which to assay said sample;

(b) affixing on said solid matrix a urokinase-type plasminogen activator that binds to said inhibitor to form a solid phase support;

(c) admixing an aliquot of a liquid sample to be assayed with said solid phase support to form a solid-liquid phase admixture;

(d) maintaining said admixture for a predetermined time sufficient for said urokinase-type plasminogen activator to bind to said inhibitor present in said sample, to form a solid phase-bound inhibitor-reagent complex;

(e) separating said solid and liquid phases;

(f) admixing an aqueous liquid solution of a polyclonal receptor that binds to said inhibitor portion of said inhibitor reagent complex bound on said solid support to form a second solid-liquid phase admixture;

(g) maintaining said second solid-liquid phase admixture for a predetermined time sufficient for said polyclonal receptor to bind to said inhibitor present in said complex;

(h) separating the solid and liquid phases of said second solid-liquid phase admixture; and (i) determining the quantity of said polyclonal receptor that bound to said inhibitor and thereby determining the quantity of inhibitor.

* * * * *

UNITED STATES PATENT AND TRADEMARK OFFICE
CERTIFICATE OF CORRECTION

PATENT NO. : 4,791,068
DATED : December 13, 1988
INVENTOR(S) : Loskutoff, et al

It is certified that error appears in the above-identified patent and that said Letters Patent is hereby corrected as shown below:

In column 1, line 7, please insert:

--This invention was made with government support under Contract Nos. HL22289 and HL16411 by the National Institutes Health. The government has certain rithts in the invention--.

Signed and Sealed this

Nineteenth Day of December, 2000

Attest:

Q. TODD DICKINSON

*Attesting Officer*            *Commissioner of Patents and Trademarks*